United States Patent
Gust, Jr. et al.

(10) Patent No.: US 8,669,359 B2
(45) Date of Patent: Mar. 11, 2014

(54) ELECTRICALLY CONDUCTING PORPHYRIN AND PORPHYRIN-FULLERENE ELECTROPOLYMERS

(75) Inventors: John Devens Gust, Jr., Mesa, AZ (US); Paul Anthony Liddell, Apache Junction, AZ (US); Miguel Andres Gervaldo, Cordoba (AR); James Ward Bridgewater, Mesa, AZ (US); Bradley James Brennan, Omaha, NE (US); Thomas Andrew Moore, Scottsdale, AZ (US); Ana Lorenzelli Moore, Scottsdale, AZ (US)

(73) Assignee: Arizona Board of Regents for and on behalf of Arizona State University, Scottsdale, AZ (US)

( * ) Notice: Subject to any disclaimer, the term of this patent is extended or adjusted under 35 U.S.C. 154(b) by 416 days.

(21) Appl. No.: 12/552,187

(22) Filed: Sep. 1, 2009

(65) Prior Publication Data

US 2010/0065123 A1 Mar. 18, 2010

Related U.S. Application Data

(63) Continuation of application No. PCT/US2008/055545, filed on Feb. 29, 2008.

(60) Provisional application No. 60/892,757, filed on Mar. 2, 2007.

(51) Int. Cl.
C07D 487/22 (2006.01)
(52) U.S. Cl.
USPC .......................................................... 540/145
(58) Field of Classification Search
USPC .......................................................... 540/145
See application file for complete search history.

(56) References Cited

FOREIGN PATENT DOCUMENTS

| JP | 63-135387 | 6/1988 |
| JP | 01-006949 | 1/1989 |
| JP | 2003-031832 | 1/2003 |
| WO | WO 2008/109467 | 9/2008 |

OTHER PUBLICATIONS

Ichihara et al. "New and efficient synthesis of oligomeric porphyrins via stepwise nucleophilic substitution of aminoporphyrins to cyanuric chloride." 1995, Chemistry Letters, 8, 631-632 (abstract included only).*
International Search Report and Written Opinion dated Jun. 17, 2006 for PCT/US2008/055545, filed Feb. 29, 2008 (14 pages).
Basu, J. and K.K. Rohatgi-Mukherjee, "Photoelectrochemical characterisation of porphyrin-coated electrodes," Solar Energy Materials 21: 317-325 (1991).

Bedioui, F. and J. Devynck, "Immobilization of Metalloporphyrins in Electropolymerized Films: Design and Applications," Acc. Chem. Res. 28: 30-36 (1995).
Bettelheim, A. et al., "Electrochemistry of various substituted aminophenyl iron porphyrins," Journal of Electroanalytical Chemistry, 266: 93-108 (1989).
Bettelheim, A. et al., "Electrocatalysis of dioxygen reduction in aqueous acid and base by multimolecular layer films of electropolymerized cobalt tetra(o-aminophenyl)porphyrin," Journal of Electroanalytical Chemistry, 217: 271-286 (1987).
Bettelheim, A. et al., "Electrochemical Polymerization of Amino-, Pyrrole-, and Hydroxy-Substituted Tetraphenylporphyrins," Inorganic Chemistry, 26: 1009-1017 (1987).
Boyd, P.D.W. and C.A. Reed, "Fullerene-Porphyrin Constructs," Accounts of Chemical Research 38(4): 235-242 (2005).
Bruti, E. M. et al., "Electropolymerization of Tetrakis (o-aminophenyl)porphyrin and Relevant Transition Metal Complexes from Aqueous Solution. The Resulting Modified Electrodes as Potentiometric Sensors,". Electroanalysis 11(8): 565-572 (1999).
Duanmu, C.-S. et al., "Synthesis of Covalently-linked Linear Donor-Acceptor Copolymers Containing Porphyrins and Oligothiophenes," Chinese Journal of Chemistry 22: 779-781 (2004).
Feng, X. and M.O. Senge, "An efficient synthesis of highly functionazlied asymmetric porphyrins with organolithium reagents," J. Chem. Soc., Perkin Trans. 1: 1030-1038 (2001).

(Continued)

Primary Examiner — Brian McDowell
(74) Attorney, Agent, or Firm — Fish & Richardson P.C.

(57) ABSTRACT

Compounds with aryl ring(s) at porphyrin meso position(s) bearing an amino group in position 4 relative to the porphyrin macrocycle, and at least one unsubstituted 5 (hydrogen-bearing) meso position with the 10-, 15-, and/or 20-relationship to the aryl ring bearing the amino group, and metal complexes thereof, feature broad spectral absorption throughout the visible region. These compounds are electropolymerized to form electrically conducting porphyrin and porphyrin-fullerene polymers that are useful in photovoltaic applications. The structure of one such electrically conducting porphyrin polymer is shown below.

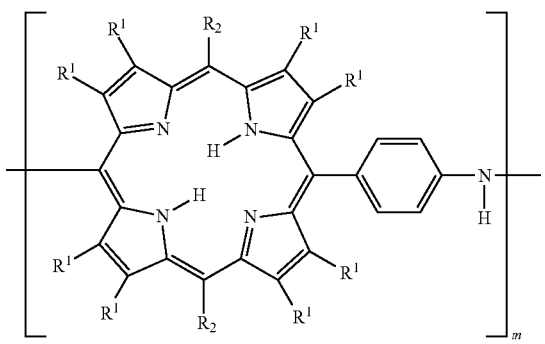

2 Claims, 7 Drawing Sheets

(56) References Cited

OTHER PUBLICATIONS

Feng, X.. and M.O. Senge, "Facile and Efficient Synthesis of Functionalized Asymmetric Porphyrins with Organolithium Reagents," Proceedings of the Fourth International Conference on Synthetic Organic Chemistry (ECSOC-4), www.mdpi.org/ecsoc-4.htm, Sep. 1-30, 2000, 7 pages [accessed Dec. 11, 2009].

Fish, J.R. et al., "Synthesis and Electrochemistry of Conductive Copolymeric Porphyrins," Chem. Mater. 4: 795-803 (1992).

Griveau, S. et al., "Comparative study of electropolymerized cobalt porphyrin and phthalocyanine based films for the electrochemical activation of thiols," Journal of Materials Chemistry 12: 225-232 (2002).

Laha, J.K. et al., "A Scalable Synthesis of Meso-Substituted Dipyrromethanes," Organic Process Research & Development 7: 799-812 (2003).

Li, G. et al., "Very stable, highly electroactive polymers of zinc(II)-5,15-bisthienylphenyl porphyrin exhibiting charge-trapping effects," Polymer 46: 5299-5307 (2005).

Liddell, P.A. et al., "Porphyrin-Based Hole Conducting Electropolymer," Chem. Mater. 20: 134-142 (2008).

Lin, C.Y. et al., "Synthesis, electrochemistry, absorption and electropolymerization of aniline-ethynyl metalloporphyrins," Dalton Transactions, pp. 396-401 (2005).

Macor, K. A.. and T.G. Spiro, "Porphyrin Electrode Films Prepared by Electrooxidation of Metalloprotoporphyrins," J. Am. Chem. Soc. 105: 5601-5607 (1983).

Macor, K. A. and T.G. Spiro, "Oxidative Electrochemistry of Electropolymerized Metalloprotoporphyrin Films," Journal of Electroanalytical Chemistry 163: 223-236 (1984).

Macor, K. A. et al., "Electrochemical and Resonance Raman Spectroscopic Characterization of Polyaniline and Polyaniline-Metalloporphyrin Electrode Films," Inorganic Chemistry 26: 2594-2598 (1987).

Malinski, T. et al., "Conductive Polymeric Cu(II) Tetrakis(3-methoxy-4-hydroxyphenyl) porphyrin as a Photosensitizer in a Photoelectrochemical Cell," Advanced Materials 4: 354-357 (1992).

Maree, C. H. M. et al., "Photovoltaic effects in porphyrin polymer films and heterojunctions," Journal of Applied Physics 80: 3381-3389 (1996).

Mortimer, R. J., "Electrochromic materials," Chemical Society Reviews, 26: 147-156 (1997).

Poriel, C. et al., "Anodic oxidation and physicochemical properties of various porphyrin-fluorenes or—spirobifluroenes: Synthesis of new polymers for heterogeneous catalytic reactions," Journal of Electroanalytical Chemisty 583: 92-103 (2005).

Radziszewski, J.G., et al., "Polarized Infrared Spectra of Photooriented Matrix-Isolated Free-Base Porphyrin Isotopomers," J. Phys. Chem. 99: 14254-14260 (1995).

Savenije, T. J. and A. Goossens, "Hole transport in porphyrin thin films," Physical Review B, 64: 115323-1-115323-9 (2001).

Vail, S.A. et al., "Energy and Electron Transfer in Polyacetylene-Linked Zinc-Porphyrin—[60] Fullerene Molecular Wires," Chemistry—A. European Journal 11: 3375-3388 (2005).

Wamser, C.C. et al., "Thin films of polymeric porphyrins: interfacial and eletropolymerizations," Polymer Preprints, 37(2): 384-385 (Aug. 1996).

White, B. A. and R.W. Murray, "Electroactive porphyrin films from electropolymerized metallotetra($o$-aminophenyl)porphyrins," Journal of Electroanalytical Chemistry 189: 345-352 (1985).

Wiehe, A., "Lead structures for applications in photodynamic therapy. Part 1: Synthesis and variation of $m$-THPC (Temoporfin) related amphiphilic $A_2BC$-type porphyrins," Tetrahedron 61: 5535-5564 (2005).

Wöhrle, D., "Porphyrins, phthalocyanines and related systems in polymer phases," Journal of Porphyrins and Phthalocyanines 4: 418-424 (2000).

Yu, L. et al., "Excited-State Energy-Transfer Dynamics in Self-Assembled Triads Composed of Two Porphyrins and an Intervening Bis(dipyrrinato)metal Complex," Inorg. Chem. 42: 6629-6647 (2003).

Zhang, Y., "DFT study on the influence of $meso$-phenyl substitution on the geometric, electronic structure and vibrational spectra of free base porphyrin," Chem. Phys. 315: 201-213 (2005).

Zuh, B.-K. et al., "Enhancing the photoconductivity of polyimides by incorporating intrinsic chromosome units," Polyimides and Other High Temperature Polymers 3: 423-437 (2005).

* cited by examiner

ELECTRICALLY CONDUCTING PORPHYRIN AND PORPHYRIN-FULLERENE ELECTROPOLYMERS

CROSS-REFERENCE TO RELATED APPLICATIONS

This application is a continuation of, and claims priority under 35 U.S.C. 120 from, International Application No. PCT/US2008/055545, filed Feb. 29, 2008, which claimed priority under 35 U.S.C. 119(e)(1) from U.S. Provisional Application Ser. No. 60/892,757, filed Mar. 2, 2007. Both priority applications are incorporated herein in their entirety.

STATEMENT OF GOVERNMENT INTEREST

The invention was made with government support under Grant No. DE-FG02-03ER15393 awarded by United States Department of Energy. The government has certain rights in the invention.

FIELD OF THE INVENTION

This description relates to electropolymerizable monomers with fullerene and porphyrin subunits, polymers produced by electrooxidation of the monomers, and use of the polymers in photovoltaic devices.

BACKGROUND

One of the major applications of conducting polymers is as a component of an "organic" or "bulk heterojunction" photovoltaic cell for making electricity from sunlight. Organic solar cells generally include a layer of transparent indium tin oxide (ITO) on glass, a layer of hole-conducting polymer mixed with an organic or inorganic electron-conducting phase, and a third layer of a low-work-function metal such as aluminum. Light is absorbed by the polymer in the photovoltaic cell; the resulting excitation then migrates to a phase boundary with the electron-conducting phase, and an electron is injected from the polymer. The electrons migrate to the metal through the electron-conducting phase, and holes migrate to the ITO via the polymer, generating a photocurrent.

Conducting polymers for use in organic light-emitting diodes (OLEDs) and organic conductors ("wires"), some of which may be electropolymerized, have been reported. These polymers include, for example, polyacetylenes, polyphenyleneethynylenes (PPE), polyphenylenevinylenes (PPV), polythiophenes, and polyanilines. The structural variations of these polymers are typically changes in the organic substituent groups attached to the basic polymer backbone. The substituents can change the electrical properties of the polymer, its processing and mechanical properties, and its compatibility/interfacing with other materials. Typically, it is possible to write delocalized structures for these polymers that allow conductivity through the polymer backbone. Often, some type of "doping" is required to achieve good conductivity.

Such organic photovoltaic cells have very low efficiencies (i.e., less than about 5%) due to incomplete conversion of excitons to charge separation, recombination of electrons and holes within the organic layer or at the electrodes, and a lack of efficient light absorption throughout the solar spectral range. The lack of electron acceptors covalently bonded to the polymer strands can lead to inefficient conversion of excitons to charge separation, rapid charge recombination, high concentrations of carriers at interface areas (leading to increased recombination), the need to prepare bicontinuous phases of polymer and fullerene or other electron carriers (which adds to processing requirements), and the need to use excessive amounts of the electron transport phase.

SUMMARY

In one aspect, a compound has the formula:

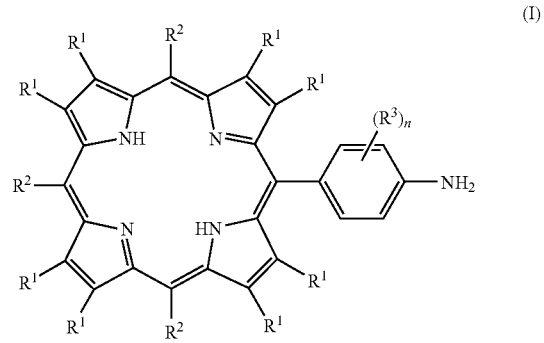

(I)

with the substituents described below.

Each $R^1$ is independently —H, -alkyl, or alkenyl. $R^1$ is optionally substituted with one or more groups which are each independently R, or any two $R^1$ on adjacent carbon atoms form a fused phenyl group which is optionally substituted by one or more R groups.

Each $R^2$ is independently —H, -alkyl, -aryl, or -heteroaryl. The alkyl or heteroaryl is optionally substituted with one or more R groups or one or more $R^F$ groups, and the aryl is optionally substituted with one or more R' groups.

Each $R^3$ is independently -halogen, -alkyl, -aryl, -cycloalkyl, -heterocyclyl, or -heteroaryl. Each $R^3$ is optionally substituted with one or more R groups, and n is 0, 1, 2, 3, or 4.

Each R is independently -halogen, -alkyl, -aryl, -cycloalkyl, -heterocyclyl, -heteroaryl, —$OR^4$, —$SR^4$, —$N(R^4)_2$, —$C(O)R^4$, —$C(O)OR^4$, —$C(O)N(R^4)_2$, —$OC(O)R^4$, —$OC(O)OR^4$, —$OC(O)N(R^4)_2$, —$N(R^4)C(O)R^4$, —$N(R^4)C(O)OR^4$, —$N(R^4)C(O)N(R^4)_2$, —$S(O)_2R^4$, —$S(O)_2N(R^4)_2$, or —$S(O)_2OR^4$.

Each R' is independently -halogen, -alkyl, -aryl, -cycloalkyl, -heterocyclyl, -heteroaryl, —$SR^4$, —$N(R^4)_2$, —$C(O)R^4$, —$C(O)OR^4$, —$C(O)N(R^4)_2$, —$OC(O)R^4$, —$OC(O)OR^4$, —$OC(O)N(R^4)_2$, —$N(R^4)C(O)R^4$, —$N(R^4)C(O)OR^4$, ($R^4$)$C(O)N(R^4)_2$, —$S(O)_2R^4$, —$S(O)_2N(R^4)_2$, —$S(O)_2OR^4$, or —$R^F$.

$R^F$ is -L-cycloalkyl or -L-heterocyclyl. The cycloalkyl and heterocyclyl are optionally substituted with $R^5$ groups.

Each $R^4$ is independently —H or -alkyl.

Each $R^5$ is independently R, or two $R^5$ groups on adjacent carbon atoms form a fused aryl, -heteroaryl-, -heterocyclyl-, -cycloalkyl- or -fullerenyl-.

L is a bond, -$L^1$-, -$L^1$-alkyl-, or -$L^1$-alkyl-$L^1$-, and $L^1$ is —C(O)O—, —OC(O)—, —N($R^4$)C(O)—, —C(O)N($R^4$)—, —O—, —S—, —N($R^4$)—, —OC(O)O—, —OC(O)N($R^4$)—, —N($R^4$)C(O)O—, or —N($R^4$)C(O)N($R^4$)—.

An embodiment of formula (I) includes:
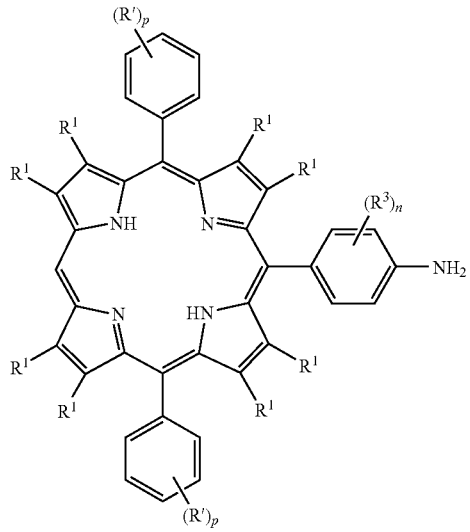
(II)
in which p is independently 0, 1, 2, 3, 4, or 5.
When n=0, formula (II) becomes:
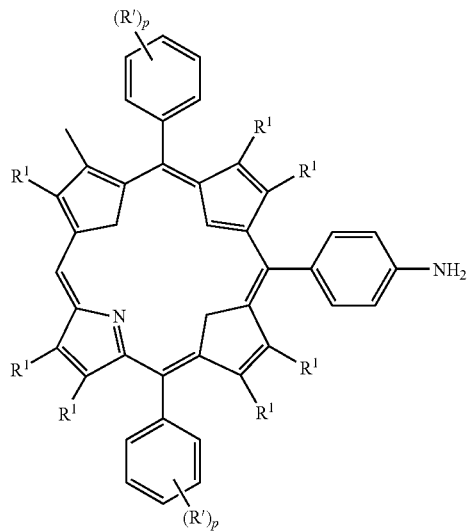
(VI)
In some implementations, formula (II) includes:
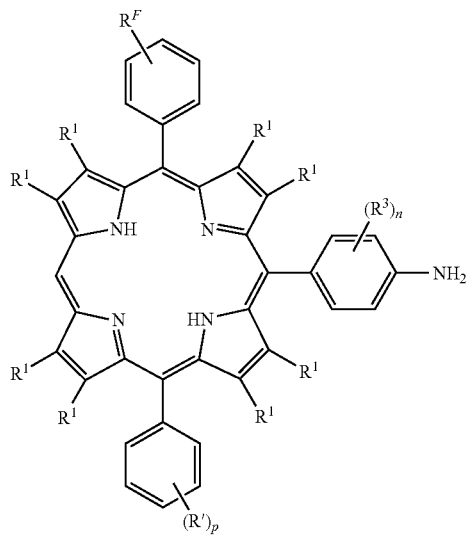
(III)
When n=0, formula (III) becomes:
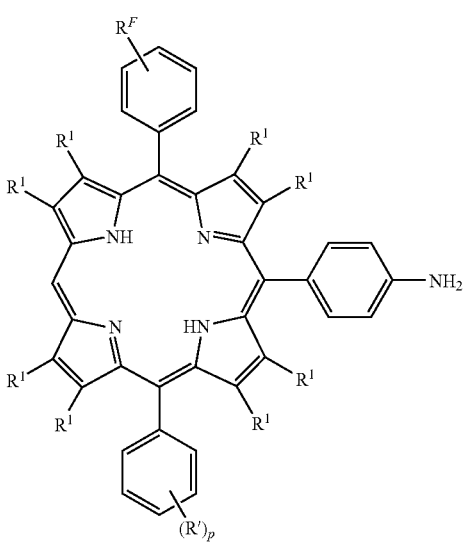
(VII)

In some implementations, formula (III) includes:

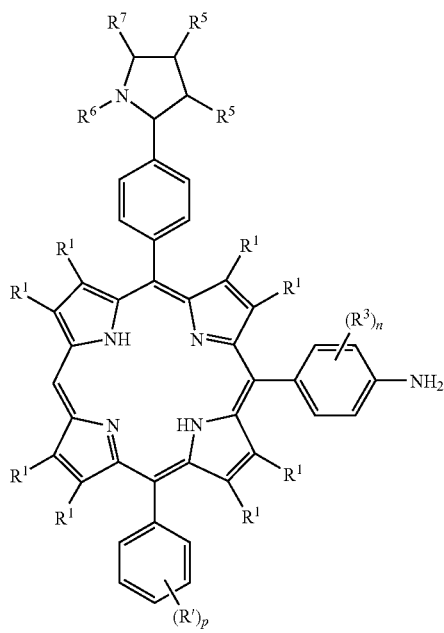

in which
R$^6$ is —H, -alkyl, —C(O)R$^4$, —C(O)OR$^4$, —C(O)N(R$^4$)$_2$, —S(O)$_2$R$^4$, —S(O)$_2$N(R$^4$)$_2$, or —S(O)$_2$OR$^4$, and
R$^7$ is —H, -halogen, -alkyl, -aryl, -cycloalkyl, -heterocyclyl, -heteroaryl, —OR$^4$, —SR$^4$, —N(R$^4$)$_2$, —C(O)R$^4$, —C(O)OR$^4$, C(O)N(R$^4$)$_2$, —OC(O)R$^4$, —OC(O)OR$^4$, —OC(O)N(R$^4$)$_2$, —N(R$^4$)C(O)R$^4$, —N(R$^4$)C(O)OR$^4$, —N(R$^4$)C(O)N(R$^4$)$_2$, —S(O)$_2$R$^4$, —S(O)$_2$N(R$^4$)$_2$, —S(O)$_2$OR$^4$, or R$^F$.

When n=0, formula (IV) becomes:

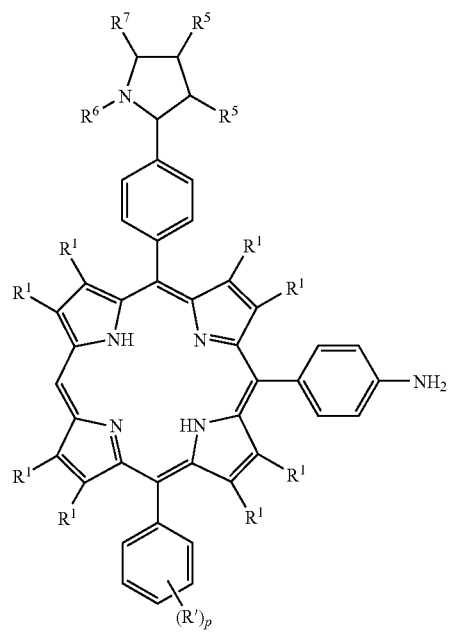

In embodiments of formulas (IV)-(V), the two R$^5$ groups on adjacent carbon atoms can form a fused fullerenyl group. When the two R$^5$ groups on adjacent carbon atoms form a fused C$_{60}$ fullerenyl group, formula (IV) is referred to as formula (VIII), and formula (V) is referred to as formula (IX).

In some embodiments of formulas (I)-(IX), p is 0, 1, 2, or 3, and each R' is independently -halogen or -alkyl.

In some implementations, the compound of formulas (I)-(IX) is complexed to a metal ion. The metal ion can be an ion of Na, Li, K, Zn, Cd, Cu, Co, Ni, Ru, Rh, Hg, Pd, Pt, Mg, Ca, Fe, Mn, Cr, Al, Ga, In, V, Sn, or Pb.

In another aspect, a polymer includes porphyrin monomers, and the porphyrin monomers form the backbone of the polymer.

In one implementation, the polymer has the formula:

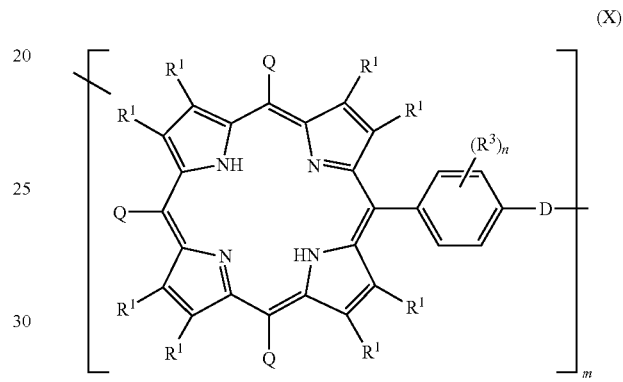

in which:
m is an integer greater than 2;
D is NH;
each Q is independently a bond or R$^2$;
and each monomer is bonded to at least one other monomer through a Q-D bond. All other substituents are as described above.

In some implementations, formula (X) includes:

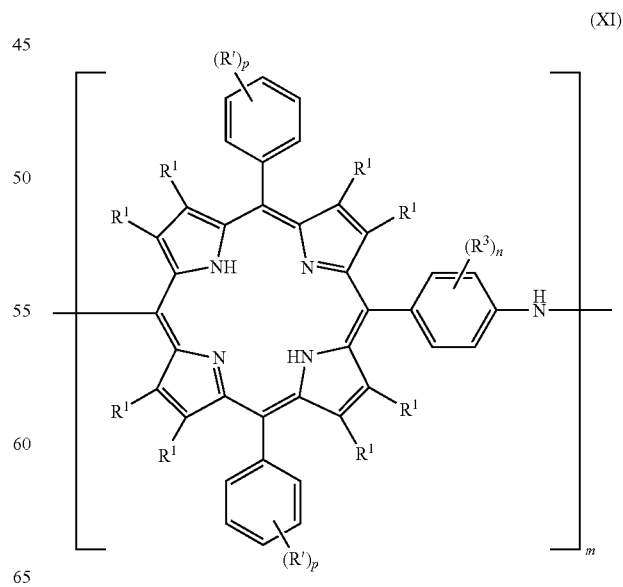

in which each p is independently 0, 1, 2, 3, 4, or 5.

In some implementations, formula (XI) includes:

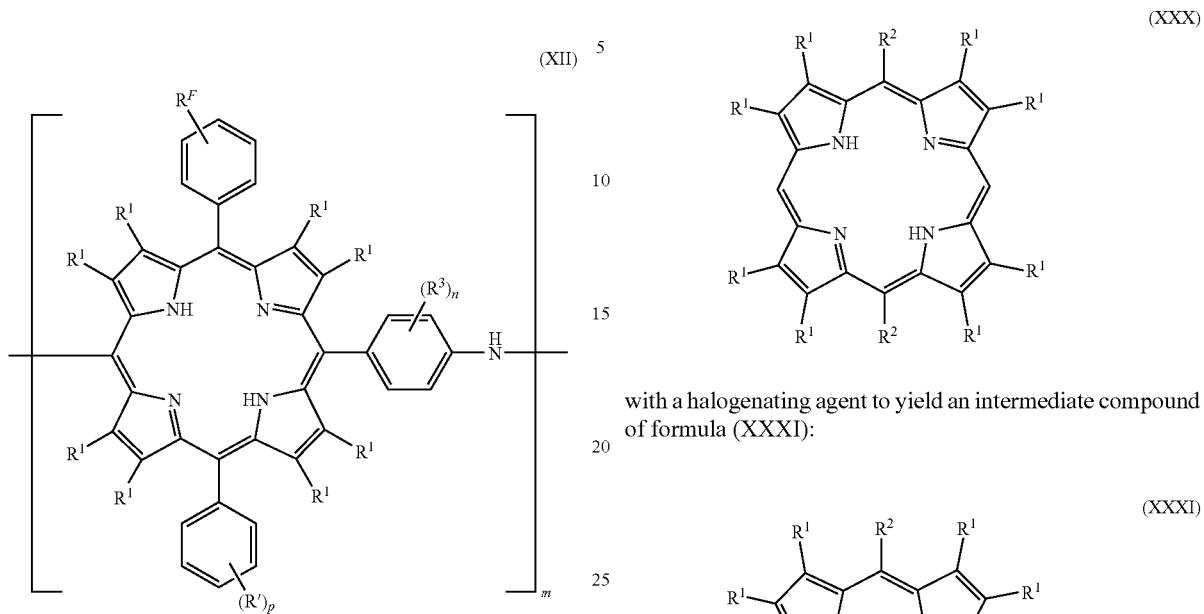

In an embodiment of formula (XII), $R^F$ is -heterocyclyl substituted with two $R^5$ groups. When the two $R^5$ groups on adjacent carbon atoms form a fused fullerenyl group, such polymers are referred to as formula (XIII). When the two $R^5$ groups on adjacent carbon atoms form a fused $C_{60}$ fullerenyl group, such polymers are referred to as formula (XIV).

In some implementations of formulas (X)-(XIV), p is 0, 1, 2, or 3, and each R' is independently -halogen or -alkyl.

In some embodiments of formulas (X)-(XIV), m is an integer greater than 2 and less than 10,000, greater than 2 and less than 1000, greater than 2 and less than 500, greater than 2 and less than 250, or greater than 2 and less than 100.

In some implementations, one or more monomer units of the polymer in formulas (X)-(XIV) is complexed to a metal ion. In some embodiments, the metal ion is an ion of Na, Li, K, Zn, Cd, Cu, Co, Ni, Ru, Rh, Hg, Pd, Pt, Mg, Ca, Fe, Mn, Cr, Al, Ga, In, V, Sn, or Pb.

In another aspect, a method of synthesizing a compound of the formula:

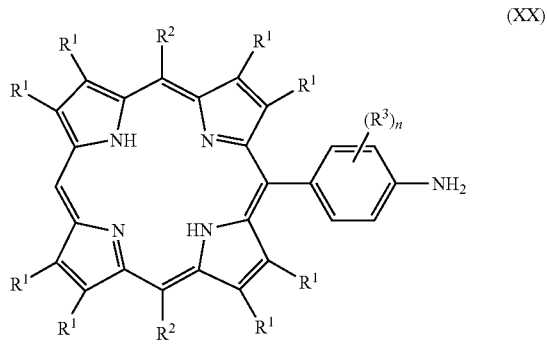

includes contacting a compound of formula (XXX):

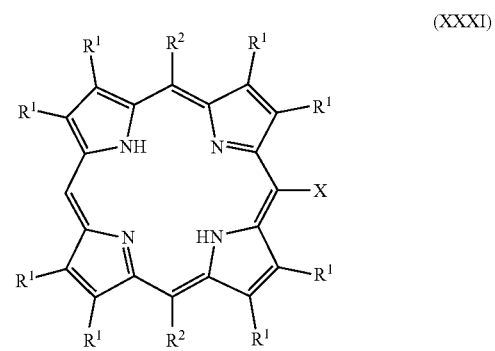

with a halogenating agent to yield an intermediate compound of formula (XXXI):

(XXXI)

[porphyrin structure with X substituent]

in which X is a halogen. The compound of formula (XXXI) is contacted with a compound of formula (XXXII):

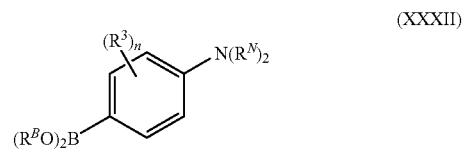

in the presence of a palladium catalyst and a base. In formula (XXXII), each $R^B$ is —H or -alkyl, or both $R^B$ taken together with the oxygen atoms to which they are attached form a heterocyclic group;

each $R^N$ is —H, —C(O)$R^{10}$, or —S(O)$_2R^{10}$; and $R^{10}$ is -alkyl, -aryl, or -alkyl-aryl.

Other substituents are as described above.

In some implementations, the halogenating agent is N-bromosuccinimide, N-chlorosuccinimide, or N-iodosuccinimide. In some embodiments, X is iodo, bromo, or chloro.

In some embodiments, the palladium catalyst is a Pd(0) or Pd(II) catalyst. The Pd(0) catalyst can be, for example, palladium metal, Pd(PPh$_3$)$_4$, Pd$_2$(dba)$_3$ and a phosphine ligand (e.g., t-Bu$_3$P, t-Bu$_2$PMe, PPh$_3$, PCy$_3$, etc.), or Pd(t-Bu$_3$P)$_2$. The Pd(II) catalyst can be, for example, Pd(OAc)$_2$, PdCl$_2$(PPh$_3$)$_2$, PdCl$_2$(dppe), PdCl$_2$(dppp), or PdCl$_2$(dppf).

In some embodiments, the base is sodium fluoride, potassium fluoride, sodium hydroxide, potassium hydroxide, potassium carbonate, sodium carbonate, cesium carbonate, potassium phosphate, sodium methoxide, sodium ethoxide, sodium isopropoxide, sodium tert-butoxide, potassium methoxide, potassium ethoxide, potassium isopropoxide, or potassium tert-butoxide.

In one aspect, a method of synthesizing a polymer of one or more compounds of formula (XX) includes preparing a solution of one or more compounds of formula (XX) in a solvent, and providing an electrical potential to the solution.

In some implementations, the electrical potential is a constant oxidizing potential. The electrical potential can be cycled from about −1.0 V to 2.0 V, from about −0.5 V to 1.75 V, or from about 0.0 V to 1.50 V.

The solvent can be an alkyl nitrile, aryl nitrile, chlorinated hydrocarbon, alkyl ether, or any mixture thereof. In some cases, the solvent is acetonitrile, diethyl carbonate, dimethyl carbonate, 1,3-dioxolane, methyl acetate, ethyl acetate, 1-methyl-2-pyrrolidinone, tetrahydrofuran, propylene carbonate, ethylene carbonate, dichloromethane, N,N-dimethylformamide, dimethylsulfoxide, N,N-dimethylacetamide, or a mixture thereof.

In some cases, the solution includes an electrolyte. The electrolyte can be a tetrafluoroborate, hexafluorophosphate, halide, or perchlorate salt. The tetrafluoroborate, hexafluorophosphate, halide, or perchlorate salt preferably has a tetraalkylammonium or alkali metal cation. Examples of electrolytes include, but are not limited to, lithium perchlorate, tetrabutylammonium tetrafluoroborate, or tetrabutylammonium hexafluorophosphate.

In some implementations, a method of synthesizing a polymer of one or more compounds of formula (XX) includes providing a working electrode, a counter electrode, and optionally, a reference electrode. The working electrode can be, for example, indium tin oxide (ITO) conducting glass, fluorinated tin oxide (FTO) conducting glass, glassy carbon, platinum, gold, silver, or other non-reactive metals. The counter electrode may be optionally separated from the solution with a glass frit or similar barrier. The counter electrode can include noble metals or graphite. For example, a counter electrode can include silver wire or platinum wire. In some cases, a reference electrode is, for example, a standard hydrogen electrode (E=0.000V), saturated calomel electrode (SCE) (E=−0.247V), copper-copper(II) sulfate electrode (E=−0.318V), or silver chloride electrode (Ag/AgCl; E=−0.225V saturated).

One aspect includes a polymer prepared according to the any of the methods described above. In some cases, the polymer is prepared from two or more different monomers of formula (XX).

Another aspect includes a photovoltaic device with a conductive substrate and a polymer described above and/or prepared according to the any of the methods described above. The polymer can be electropolymerized in one or more layers on the conductive substrate. The conductive substrate can be an electrode of the photovoltaic device. In some implementations, the conductive substrate is indium tin oxide conducting glass (ITO), fluorinated tin oxide conducting glass (FTO), glassy carbon, platinum, gold, silver, or other non-reactive metal. In certain implementations, the photovoltaic device is a solid film solar cell or a redox-solution-containing solar cell.

In one aspect, a method of forming a metal complex of the compound of any one of formulas (I)-(IX) includes the steps of contacting the compound with a metal salt such as an acetate or halide salt. The acetate salt can be, for example, zinc acetate, cobalt acetate, iron acetate, or copper acetate. The halide salt can be, for example, zinc chloride, cobalt chloride, iron chloride, or copper chloride.

In another aspect, a method of forming a polymer of any one of formulas (X)-(XII) in which one or more of the monomer units is complexed to a metal ion includes contacting the polymer with a metal salt such as an acetate or halide salt. The acetate salt can be, for example, zinc acetate, cobalt acetate, iron acetate, or copper acetate. The halide salt can be, for example, zinc chloride, cobalt chloride, iron chloride, or copper chloride.

Porphyrin electropolymers described herein provide efficient hole conduction through the conducting polymer that contains the porphyrin macrocycle in its backbone. Porphyrin-fullerene electropolymers and other polymers made from molecular dyad monomers inhibit incomplete conversion of excitons to charge separation due to recombination during exciton migration by carrying out charge separation at the site of light absorption. The recombination of charges is thought to be inhibited due to the inherently long lifetime of porphyrin-fullerene charge separation, thus reducing the formation of cut-off "islands" of conducting phases, providing an electron-blocking, hole-transport layer attached to a transparent electrode, and eliminating the concentration of charges at a severely limited amount of interface between conducting phases. In addition, a mechanism is provided, via substitution on the porphyrin, for tuning the absorption spectrum of the polymer to better utilize the solar spectrum.

Porphyrin and porphyrin-fullerene electropolymers described herein are electrically conducting and absorb light strongly in the UV and visible spectral regions. These polymers are readily prepared with or without metal atoms in each porphyrin unit, and can be used as materials in solar photovoltaic cells, such as solid film solar cells and redox-solution-containing solar cells, based on organic materials. Embodiments of photovoltaic devices with the described electropolymers are advantageously low cost and easy to fabricate and process. The polymers can be fabricated on flexible materials. They have a wide acceptance angle for light and provide high efficiency conversion of light to electrical power in the absence of rare chemical elements.

DETAILED DESCRIPTION

Figure 1:
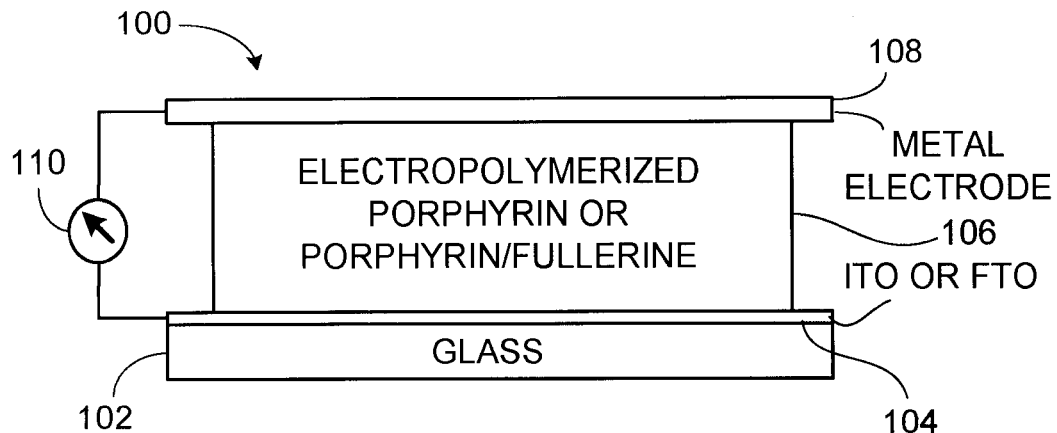
FIG. 1 is a schematic view of a solid film solar cell.

Synthesis of porphyrin monomers and metal complexes thereof, electropolymerization of these monomers to form electrically conducting polymers with a porphyrin macrocycle as part of the polymer backbone, and uses of these materials are described herein. Porphyrin macrocycles used to form electropolymers described herein can include aryl ring(s) at porphyrin meso position(s) bearing an amino group in position 4 relative to the porphyrin macrocycle, and at least one unsubstituted (hydrogen-bearing) meso position with the 10-, 15- and/or 20-relationship to the aryl ring bearing the amino group. As an example, structure 1 shows a metal complex of a standard porphyrin ring and a 5,15 relationship of the substituent-free and aminophenyl-bearing meso-positions. Compound 2 is a non-fullerene-containing embodiment of structure 1, and compound 3 is a fullerene-containing embodiment of structure 1. In some embodiments, the porphyrin is a free base porphyrin.

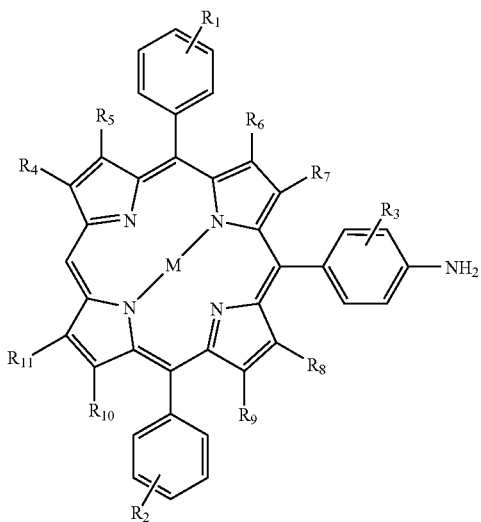

1

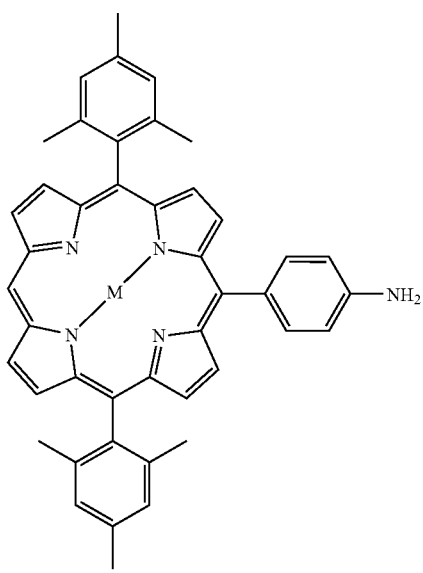

2

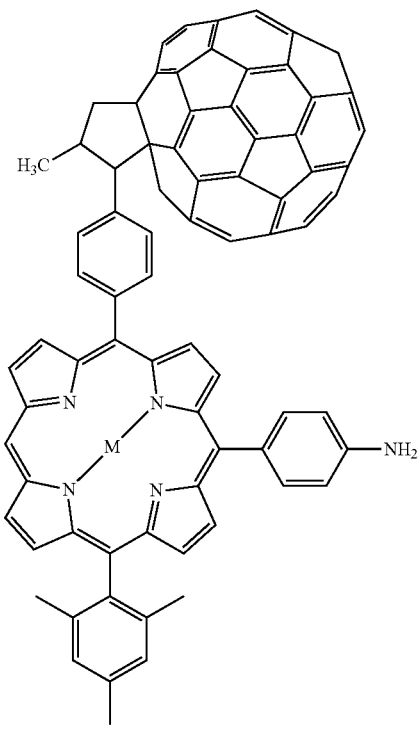

3

The term "alkenyl," as used herein, means a straight or branched chain hydrocarbon containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl," as used herein, means a straight or branched chain hydrocarbon. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. In some embodiments, an alkyl group is a —$C_1$-$C_6$ alkyl group.

The term "aryl," as used herein, means phenyl or a bicyclic aryl or a tricyclic aryl. The bicyclic aryl is naphthyl, or a phenyl fused to a cycloalkyl, or a phenyl fused to a cycloalkenyl. The bicyclic aryl is attached to the parent molecular moiety through any carbon atom contained within the bicyclic aryl. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. The tricyclic aryl is attached to the parent molecular moiety through any carbon atom contained within the tricyclic aryl. Representative examples of tricyclic aryl ring include, but are not limited to, azulenyl, dihydroanthracenyl, fluorenyl, and tetrahydrophenanthrenyl.

The term "cycloalkyl," as used herein, means a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1] heptane, bicyclo[2.2.1]heptane, bicyclo[2.2.2]octane, bicyclo[3.2.2]nonane, bicyclo[3.3.1]nonane, and bicyclo[4.2.1] nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The term "halo" or "halogen," as used herein, means —Cl, —Br, —I or —F.

The term "haloalkyl," as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic heteroaryl. The monocyclic heteroaryl is a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any nitrogen atom contained within the bicyclic heteroaryl. Representative examples of bicyclic heteroaryl include, but are not limited to, benzimidazolyl, benzofuranyl, benzothienyl, benzoxadiazolyl, cinnolinyl, dihydroquinolinyl, dihydroisoquinolinyl, furopyridinyl, indazolyl, indolyl, isoquinolinyl, naphthyridinyl, quinolinyl, tetrahydroquinolinyl, and thienopyridinyl.

The term "heterocyclyl," as used herein, means a monocyclic heterocycle or a bicyclic heterocycle or a tricyclic heterocycle. The monocyclic heterocycle is a 3, 4, 5, 6, or 7 membered ring containing at least one heteroatom independently selected from the group consisting of O, N, and S. The 3 or 4 membered ring contains 1 heteroatom selected from the group consisting of O, N, and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a cycloalkyl, or a monocyclic heterocycle fused to a cycloalkenyl, or a monocyclic heterocycle fused to a monocyclic heterocycle, or a monocyclic heterocycle fused to a monocyclic heteroaryl. The bicyclic heterocycle is connected to the parent molecular moiety through any carbon atom or any nitrogen atom contained within the bicyclic heterocycle. Representative examples of bicyclic heterocycle include, but are not limited to 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. The tricyclic heterocycle is a bicyclic heterocycle fused to a phenyl, or a bicyclic heterocycle fused to a cycloalkyl, or a bicyclic heterocycle fused to a cycloalkenyl, or a bicyclic heterocycle fused to a monocyclic heterocycle, or a bicyclic heterocycle fused to a monocyclic heteroaryl. The tricyclic heterocycle is connected to the parent molecular moiety through any carbon atom or any nitrogen atom contained within the tricyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

The term "fused," as used herein means that the group is connected to the parent molecular moiety by two chemical bonds connecting adjacent atoms of the parent moiety and adjacent atoms of the fused group. For example, a fused phenyl group attached to a furanyl parent moiety forms a benzofuranyl group, i.e., a "fused phenyl group" is also known as a "benzo group" to those skilled in the art.

Monomers described herein have the formula:

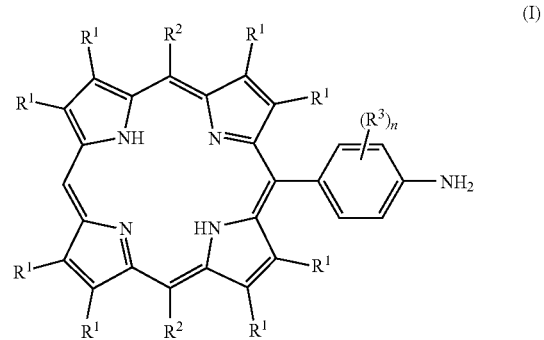

(I)

in which the substituents are described below.

Each R is independently -halogen, -alkyl, -aryl, -cycloalkyl, -heterocyclyl, -heteroaryl, —OR$^4$, —SR$^4$, —N(R$^4$)$_2$, —C(O)R$^4$, —C(O)OR$^4$, —C(O)N(R$^4$)$_2$, —OC(O)R$^4$, —OC(O)OR$^4$, —OC(O)N(R$^4$)$_2$, —N(R$^4$)C(O)R$^4$, —N(R$^4$)C(O)OR$^4$, —N(R$^4$)C(O)N(R$^4$)$_2$, —S(O)$_2$R$^4$, —S(O)$_2$N(R$^4$)$_2$, or —S(O)$_2$OR$^4$.

Each R' is independently -halogen, -alkyl, -aryl, -cycloalkyl, -heterocyclyl, -heteroaryl, —SR$^4$, —N(R$^4$)$_2$, —C(O)R$^4$, —C(O)OR$^4$, —C(O)N(R$^4$)$_2$, —OC(O)R$^4$, —OC (O)OR$^4$, —OC(O)N(R$^4$)$_2$, —N(R$^4$)C(O)R$^4$, —N(R$^4$)C(O)OR$^4$, (R$^4$)C(O)N(R$^4$)$_2$, —S(O)$_2$R$^4$, —S(O)$_2$N(R$^4$)$_2$, —S(O)$_2$OR$^4$, or R$^F$.

R$^F$ is -L-cycloalkyl or -L-heterocyclyl. The cycloalkyl and heterocyclyl are optionally substituted with R$^5$ groups.

Each R$^4$ is independently —H or alkyl.

Each R$^5$ is independently R, or two R$^5$ groups on adjacent carbon atoms form a fused aryl, -heteroaryl-, -heterocyclyl-, -cycloalkyl- or fullerenyl-.

L is a bond, -L$^1$-, -L$^1$-alkyl-, or -L$^1$-alkyl-L$^1$-, and L$^1$ is —C(O)O—, —OC(O)—, —N(R$^4$)C(O)—, —C(O)N(R$^4$)—, —O—, —S—, —N(R$^4$)—, —OC(O)O—, —OC(O)N(R$^4$)—, —N(R$^4$)C(O)O—, or —N(R$^4$)C(O)N(R$^4$)—.

In some implementations, formula (I) becomes:

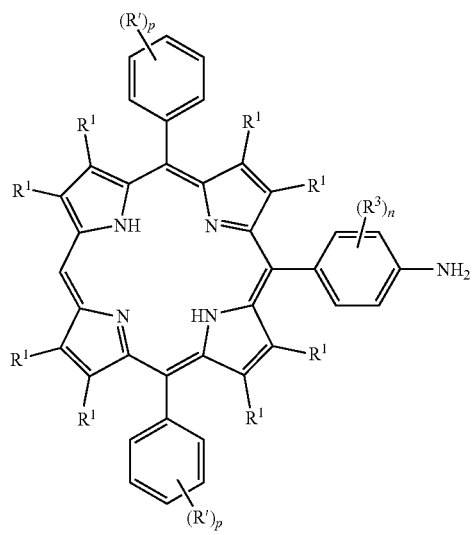

(II)

in which each p is independently 0, 1, 2, 3, 4, or 5.

When n=0, formula (II) becomes:

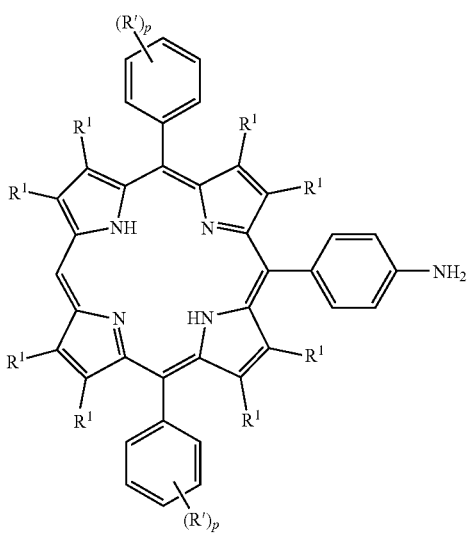

(VI)

with the various substituents as described for formula (I).

In some implementations, formula (II) becomes:

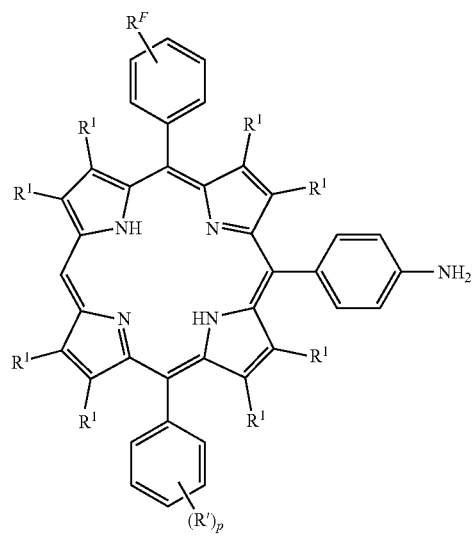

(III)

When n=0 in formula (III), the compound becomes:

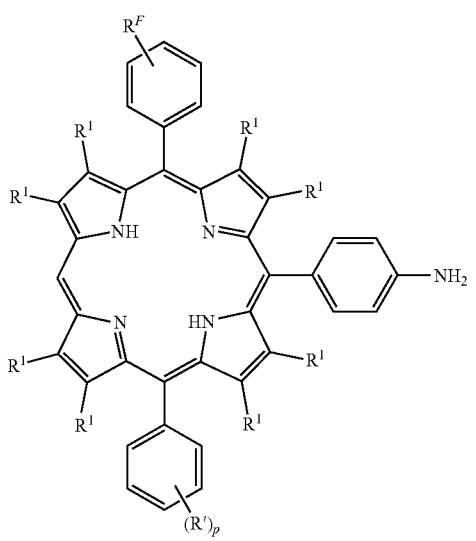

(VII)

In some implementations, formula (III) is:

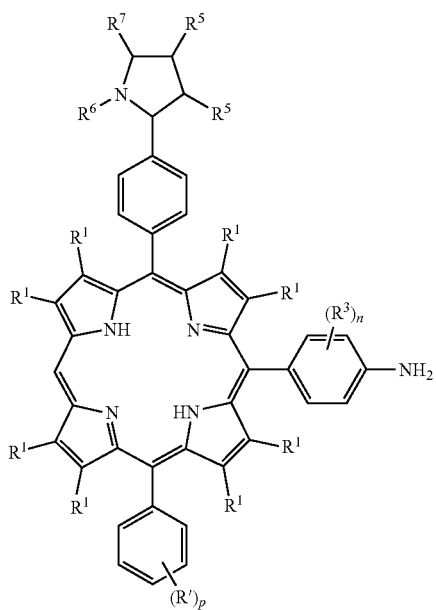

(IV)

with $R^6$ and $R^7$ defined as follows.

$R^6$ is —H, -alkyl, —C(O)R$^4$, —C(O)OR$^4$, —C(O)N(R$^4$)$_2$, —S(O)$_2$R$^4$, —S(O)$_2$N(R$^4$)$_2$, or —S(O)$_2$OR$^4$, and $R^7$ is —H, -halogen, -alkyl, -aryl, -cycloalkyl, -heterocyclyl, -heteroaryl, —OR$^4$, —SR$^4$, —N(R$^4$)$_2$, —C(O)R$^4$, —C(O)OR$^4$, —C(O)N(R$^4$)$_2$, —OC(O)R$^4$, —OC(O)OR$^4$, —OC(O)N(R$^4$)$_2$, —N(R$^4$)C(O)R$^4$, —N(R$^4$)C(O)OR$^4$, —N(R$^4$)C(O)N(R$^4$)$_2$, —S(O)$_2$R$^4$, —S(O)$_2$N(R$^4$)$_2$, —S(O)$_2$OR$^4$, or $R^F$.

When n=0, formula (IV) becomes:

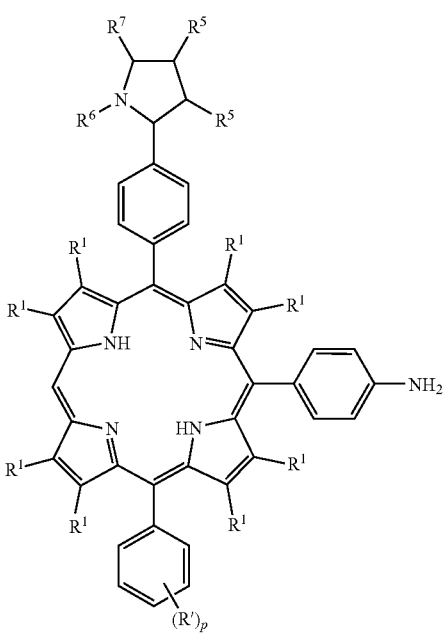

(V)

In embodiments of formulas (IV)-(V), the two $R^5$ groups on adjacent carbon atoms can form a fused fullerenyl group (e.g., a fused $C_{60}$-$C_{84}$ fullerenyl group). When the two $R^5$ groups on adjacent carbon atoms form a fused $C_{60}$ fullerenyl group, formula (IV) is referred to as formula (VIII), and formula (V) is referred to as formula (IX).

In some embodiments of formulas (I)-(IX), p is 0, 1, 2, or 3, and each R' is independently -halogen or -alkyl.

In some implementations, the compound of formulas (I)-(IX) is complexed to a metal ion. The metal ion can be an ion of Na, Li, K, Zn, Cd, Cu, Co, Ni, Ru, Rh, Hg, Pd, Pt, Mg, Ca, Fe, Mn, Cr, Al, Ga, In, V, Sn, or Pb.

The compounds and processes described herein will be better understood in connection with the following synthetic schemes which illustrate the methods by which such compounds may be prepared. Starting materials can be obtained from commercial sources or prepared by methods known to those of ordinary skill in the art.

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound.

It will also be recognized that a factor in the planning of any synthetic route in this field is the judicious choice of the protecting group used for protection of the reactive functional groups present in the compounds described herein.

A method of synthesizing a compound of the formula:

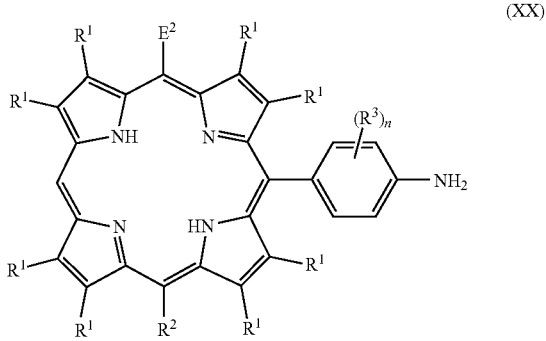

(XX)

or a metal complex thereof, includes contacting a compound of formula (XXX):

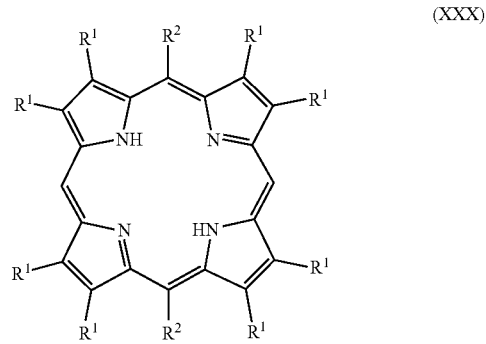

(XXX)

with a halogenating agent to yield an intermediate compound of formula (XXXI):

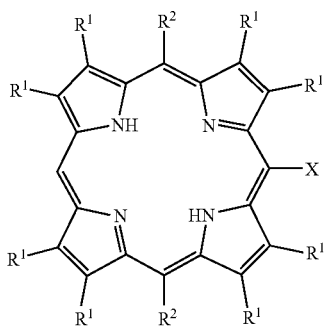

(XXXI)

in which X is a halogen. The compound of formula (XXXI) is contacted with a compound of formula (XXXII):

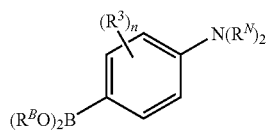

(XXXII)

in the presence of a palladium catalyst and a base. In formula (XXXII), each $R^B$ is —H or alkyl, or both $R^B$ taken together with the oxygen atoms to which they are attached form a heterocyclic group;

each $R^N$ is —H, —C(O)$R^{10}$, or —S(O)$_2R^{10}$; and $R^{10}$ is -alkyl, -aryl, or -alkyl-aryl.

Other substituents are as defined above.

In some implementations, the halogenating agent is N-bromosuccinimide, N-chlorosuccinimide, or N-iodosuccinimide. In some embodiments, X is iodo, bromo, or chloro.

In some embodiments, the palladium catalyst is a Pd(0) or Pd(II) catalyst. The Pd(0) catalyst can be, for example, palladium metal, Pd(PPh$_3$)$_4$, Pd$_2$(dba)$_3$ and a phosphine ligand (e.g. t-Bu$_3$P, t-Bu$_2$PMe, PPh$_3$, PCy$_3$, etc.), or Pd(t-Bu$_3$P)$_2$. The Pd(II) catalyst can be, for example, Pd(OAc)$_2$, PdCl$_2$(PPh$_3$)$_2$, PdCl$_2$(dppe), PdCl$_2$(dppp), or PdCl$_2$(dppf).

In some embodiments, the base is sodium fluoride, potassium fluoride, sodium hydroxide, potassium hydroxide, potassium carbonate, sodium carbonate, cesium carbonate, potassium phosphate, sodium methoxide, sodium ethoxide, sodium isopropoxide, sodium tert-butoxide, potassium methoxide, potassium ethoxide, potassium isopropoxide, or potassium tert-butoxide.

Scheme 1 illustrates a method of synthesizing the free base porphyrin corresponding to compound 2 (10-(4-aminophenyl)-5,15-bis(2,4,6-trimethylphenyl)porphyrin). Reactions shown in Scheme 1 are described in more detail in the Examples below. Suzuki coupling is performed to bind a protected aminophenyl group to the meso position of compound 6. Compounds 7 (10-(4-acetamidophenyl)-5,15-bis(2,4,6-trimethylphenyl)porphyrin) and 8 (10-(4-tert-butylphenylcarbamate)-5,15-bis(2,4,6-trimethylphenyl)porphyrin) have acetyl and tert-butyloxycarbonyl (Boc) protecting groups, respectively. The protecting groups are removed in the presence of an acid such as, for example, hydrochloric acid and/or trifluoroacetic acid, to form compound 2 (free base).

Scheme 1

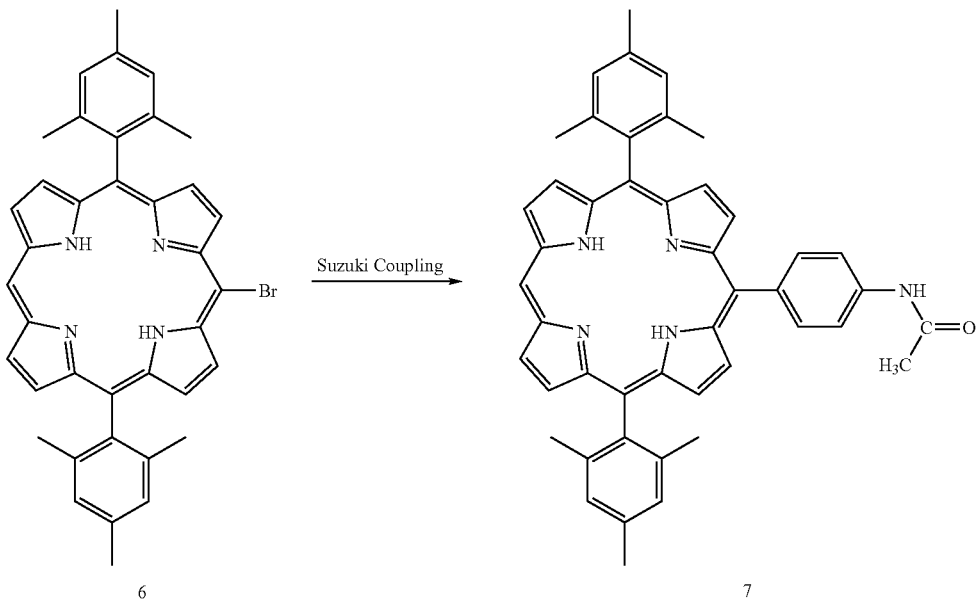

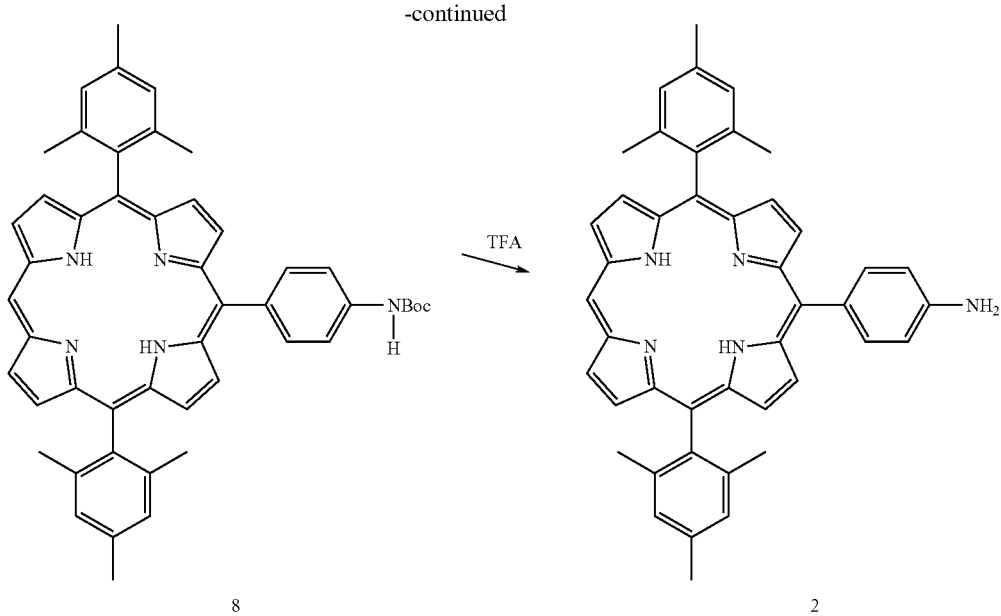

Scheme 2 illustrates a method of synthesizing the free base porphyrin corresponding to compound 3. Reactions shown in Scheme 2 are described in more detail in the Examples below. The methyl ester in compound 9 (5-(4-carboxymethyl-phenyl)-15-(2,4,6-trimethylphenyl)porphyrin) is replaced with a formyl group to form compound 10 (5-(4-formylphenyl)-15-(2,4,6-trimethylphenyl)porphyrin). After halogenation of compound 10 to form compound 11 (10-bromo-5-(4-formylphenyl)-15-(2,4,6-trimethylphenyl)porphyrin), Suzuki coupling is used to bind an aminophenyl group protected with Boc to the meso position of compound 11 to form compound 12 (5-(4-formylphenyl)-10-(4-tert-butylphenyl-carbamate)-15-(2,4,6-trimethylphenyl)porphyrin). Sarcosine and $C_{60}$ are reacted with compound 12 to form compound 13 (P—$C_{60}$ dyad), and the protecting group is removed to form compound 3 (free base).

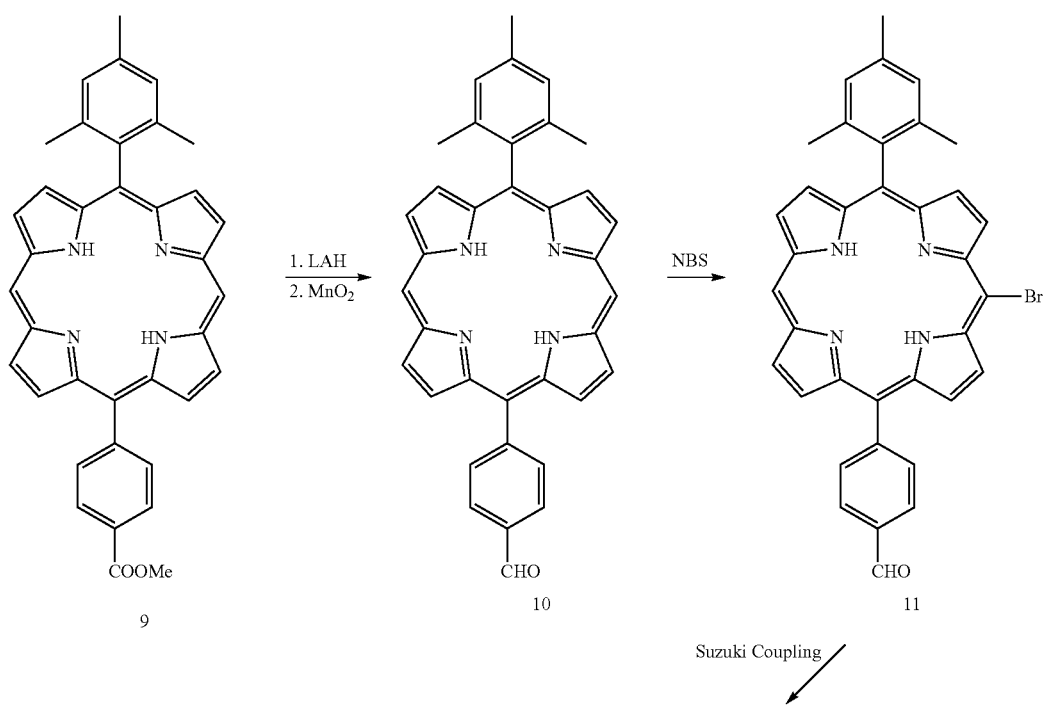

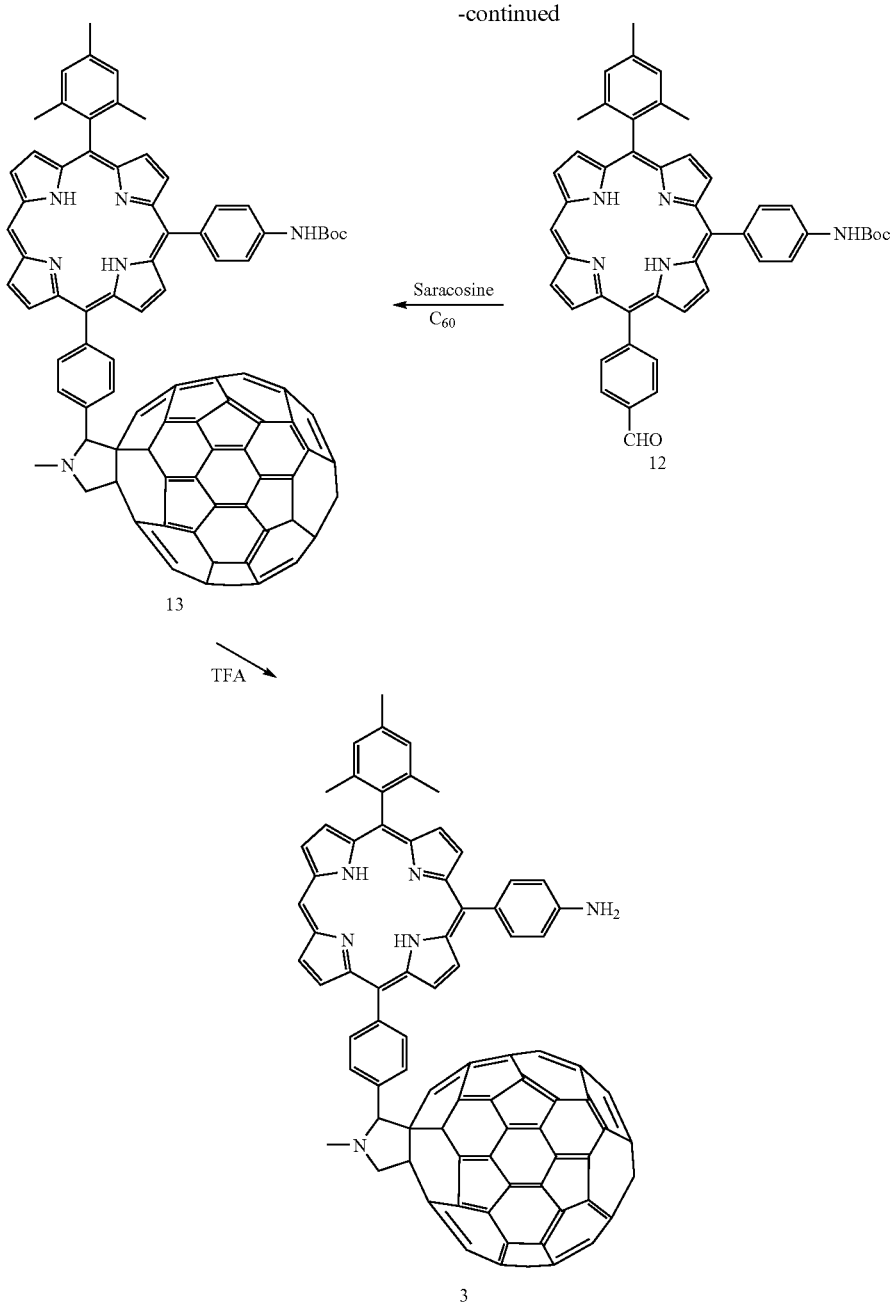

Monomers of formulas (I)-(IX) can be electropolymerized to form porphyrin electropolymers. The electropolymerization process described herein includes dissolving a monomer and a salt that will form a supporting electrolyte in a suitable solvent. A conducting working electrode such as, for example, indium tin oxide transparent conducting glass, fluorinated tin oxide conducting glass, platinum, gold, other non-reactive metals, glassy carbon, or carbon nanotube mat is immersed in the solution. A counter electrode is placed in the cell, and may be separated from the solution using a glass frit or similar barrier. A counter electrode can include graphite or noble metals such as, for example, silver wire or platinum wire. A third, reference electrode may also be included, if desired. In some cases, a reference electrode is, for example, a standard hydrogen electrode (E=0.000 V), saturated calomel electrode (SCE) (E=−0.247 V), copper-copper(II) sulfate electrode (E=−0.318 V), or silver chloride electrode (Ag/AgCl; E=−0.225 V saturated).

Electrical voltage is applied between the working and counter electrodes, and the voltage is swept back and forth over a suitable range of potentials as in cyclic voltammetry. During each sweep, a new layer of polymer is formed on the electrode. Electropolymerization may also be carried out by maintaining the potential at a suitable value. In some implementations, the electrical potential is a constant oxidizing potential. The electrical potential can be cycled from about −1.0 V to 2.0 V, from about −0.5 V to 1.75 V, or from about 0.0 V to 1.50 V.

The solvent can be an alkyl nitrile, aryl nitrile, chlorinated hydrocarbon, alkyl ether, or any mixture thereof. In some cases, the solvent is acetonitrile, diethyl carbonate, dimethyl carbonate, 1,3-dioxolane, methyl acetate, ethyl acetate, 1-methyl-2-pyrrolidinone, tetrahydrofuran, propylene carbonate, ethylene carbonate, dichloromethane, N,N-dimethylformamide, dimethylsulfoxide, N,N-dimethylacetamide, or a mixture thereof.

The electrolyte can be a tetrafluoroborate, hexafluorophosphate, halide, or perchlorate salt. The tetrafluoroborate, hexafluorophosphate, halide, or perchlorate salt preferably has a tetraalkylammonium or alkali metal cation. Examples of electrolytes include, but are not limited to, lithium perchlorate, tetrabutylammonium tetrafluoroborate, or tetrabutylammonium hexafluorophosphate.

Porphyrin monomers or macromolecules described above form the backbone of porphyrin and porphyrin-fullerene electropolymers, such that one porphyrin monomer is bonded to another to form a chain of the polymer. This porphyrin backbone structure is depicted in formulas (X)-(XVI) below. Formula (X) represents a general structure of a porphyrin or porphyrin-fullerene electropolymer:

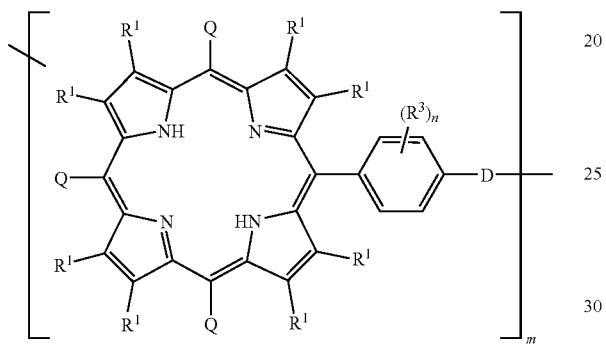

(X)

in which:
 m is an integer greater than 2;
 D is NH;
 each Q is independently a bond or $R^2$; and
 each monomer is bonded to at least one other monomer through a Q-D bond.

All other substituents are as described above. In some embodiments, m is greater than 10, greater than 50, or greater than 100, and less than 10,000.

In some implementations, formula (X) becomes:

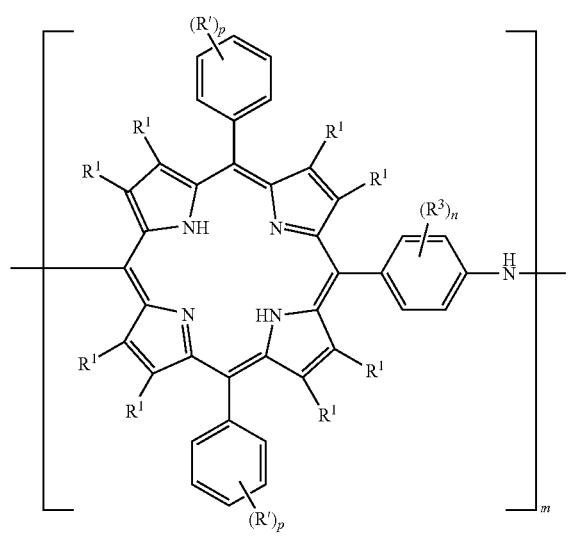

(XI)

in which each p is independently 0, 1, 2, 3, 4, or 5.

In some implementations, formula (XI) becomes:

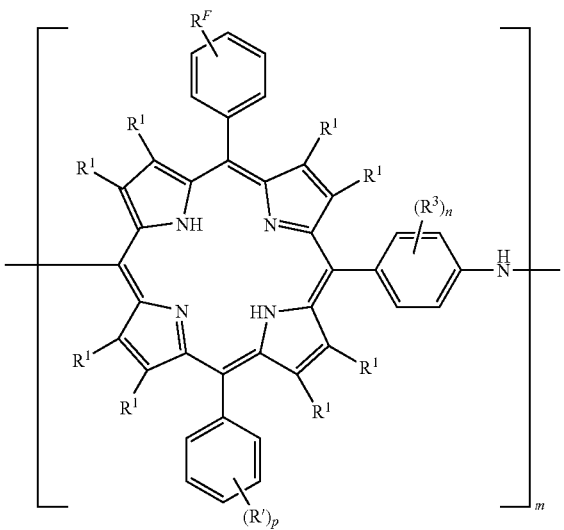

(XII)

In an embodiment of formula (XII), $R^F$ is -heterocyclyl substituted with two $R^5$ groups. When the two $R^5$ groups on adjacent carbon atoms form a fused fullerenyl group, such polymers are referred to as formula (XIII). When the two $R^5$ groups on adjacent carbon atoms form a fused $C_{60}$ fullerenyl group, such polymers are referred to as formula (XIV).

In some implementations of formulas (X)-(XIV), p is 0, 1, 2, or 3, and each R' is independently -halogen or -alkyl.

In some embodiments of formulas (X)-(XIV), m is an integer greater than 2 and less than 10,000, greater than 2 and less than 1000, greater than 2 and less than 500, greater than 2 and less than 250, or greater than 2 and less than 100.

In some implementations, one or more monomer units of the polymer formulas (X)-(XIV) is complexed with a metal ion. The metal ion can be an ion of Na, Li, K, Zn, Cd, Cu, Co, Ni, Ru, Rh, Hg, Pd, Pt, Mg, Ca, Fe, Mn, Cr, Al, Ga, In, V, Sn, or Pb.

The porphyrin electropolymers can be prepared according to any of the methods described above. In some cases, each monomer is independently a compound of formula (XX). In an example, the structure of the polymer formed from the free base porphyrin corresponding to compound 2 is understood to be as shown in formula (XV) below.

(XV)

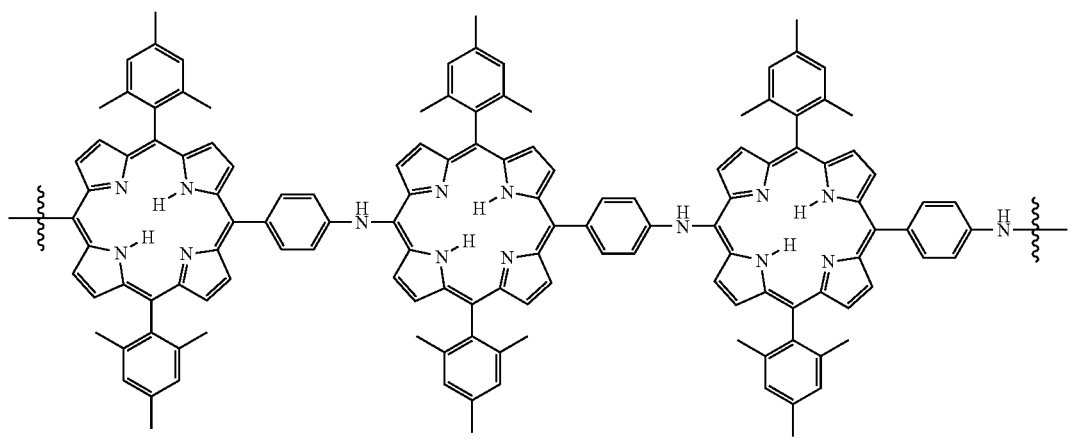

Formula (XVI) depicts a possible delocalized structure of an oxidized polymer of formula (XV).

(XVI)

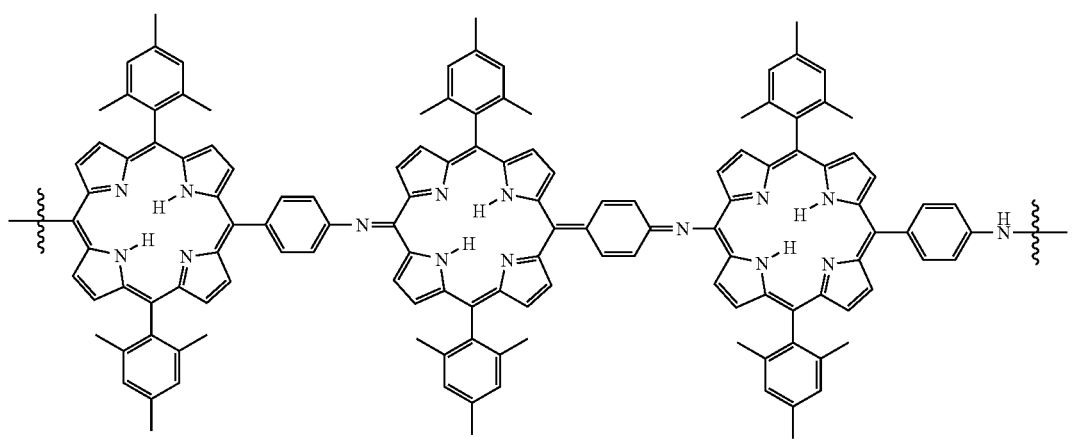

Formulas (XV) and (XVI) depict a polymer including porphyrin monomer units in which the porphyrin monomers form the backbone of the polymer.

A polymer described above and/or prepared according to the any of the methods described above can be coupled to (for example, electropolymerized or layered on) a conductive substrate. In some embodiments, the conductive substrate is indium tin oxide conducting glass (ITO), fluorinated tin oxide conducting glass (FTO), glassy carbon, platinum, gold, silver, or another non-reactive metal.

Metal complexes (or metalated forms) of formulas (X)-(XVI) can be prepared by contacting the protonated polymers of formulas (X)-(XVI) with a metal salt such as an acetate or halide salt. The acetate salt can be, for example, zinc acetate, cobalt acetate, iron acetate, or copper acetate. The halide salt can be, for example, zinc chloride, cobalt chloride, iron chloride, or copper chloride. Alternatively, metal complexes of formulas (X)-(XVI) can be prepared by electropolymerizing metal complexes of formulas (I)-(IX).

Properties of conducting porphyrin polymers described herein are particularly suited to use in applications for organic, bulk heterojunction solar cells, such as solid film solar cells and redox-solution-containing solar cells. These polymers can be electropolymerized on a transparent or semi-transparent electrode, providing enhanced electrical conductivity between the electrode and the polymer.

FIG. 1 depicts a schematic view of a solid film solar cell 100. Solar cell 100 includes substrate 102, and a conducting, transparent electrode 104 on the substrate. Electrode 104 can be, for example, ITO, FTO, carbon nanotube mats, or other suitable conductive, transparent or semi-transparent materials. A film of electropolymerized porphyrinic material 106 is grown electrochemically on electrode 104. The porphyrinic material can include one or more porphyrin or porphyrin-fullerene electropolymers, or a mixture thereof, other electropolymers, and electron transport or other additives. Electrical contact is made between the electrode 104 and the porphyrin material 106. The side of the porphyrin material 106 not in contact with electrode 104 is contacted physically and electrically with second electrode 108. Second electrode 108 can be, for example, a metal or other conductor such as platinized FTO, carbon nanotube electrodes, and polymer electrodes. Illumination of solar cell 100 results in a photovoltage and photocurrent between electrodes 104 and 108.

If porphyrinic material 106 includes only non-fullerene-containing porphyrin electropolymers (for example, the porphyrinic material is the electropolymer depicted in formula (XV)), light is absorbed by the porphyrinic material. Excitation energy migrates through the film 106 to the region near an electrode, and the polymer excited state injects a charge (e.g., an electron) into the electrode, leaving an opposite charge (e.g., a positive charge, or hole) within the electropolymer film. This second charge migrates to the interface between the electropolymer 106 and the other electrode, and is thereupon injected into that electrode. A photovoltage between the electrodes is thus established. If the two electrodes 104, 108 are connected electrically through electrical load 110, a photocurrent flows, and work is done. Creation of electron-hole pairs within the film 106 is also possible, depending upon the redox characteristics of the particular polymer(s) used.

In the presence of an electropolymer material 106 that includes both porphyrin and fullerene (e.g., a polymer made from compound 3 or its free base), light is absorbed by both the porphyrin and the fullerene chromophores within the polymer. The porphyrin excited states donate electrons to the fullerenes, and the fullerene excited sates can accept electrons from the porphyrin. In either case, a porphyrin-fullerene charge-separated state is formed. The electrons then migrate through the polymer and any associated conducting material to one electrode, and the holes migrate to the other electrode. A photovoltage between the electrodes 104 and 108 is thus established. If the two electrodes are connected electrically through an electrical load, a photocurrent flows, and work is done. Migration of excitation energy may also occur within the electropolymer.

Figure 2:
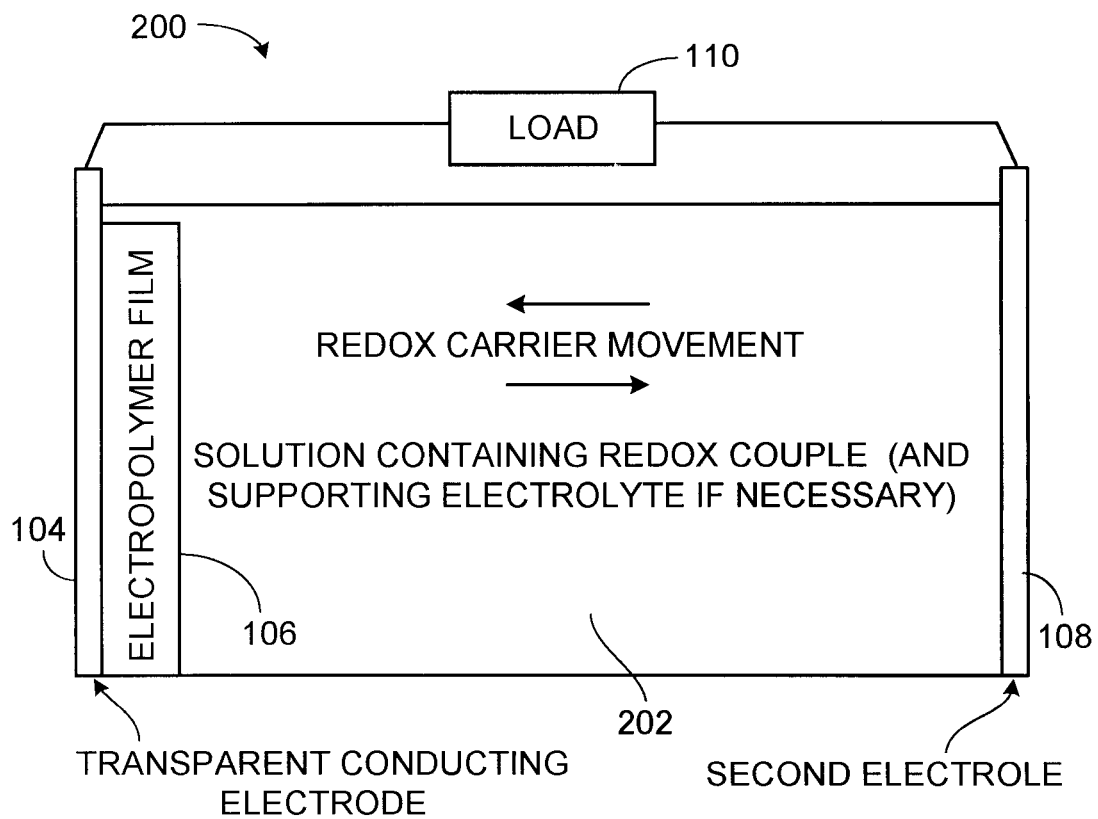
FIG. 2 is a schematic view of a redox-solution-containing solar cell.

FIG. 2 is a schematic diagram of a redox-solution-containing solar cell 200. A film of electropolymerized porphyrinic material 106, including a porphyrin electropolymer, a porphyrin-fullerene electropolymer, or a mixture thereof, with or without other electropolymers and additives, is grown electrochemically on a conducting, transparent or semi-transparent electrode 104, which is one electrode of solar cell 200. Electrode 104 can include ITO, FTO, carbon nanotube mats, or other suitable conductive, transparent or semi-transparent materials, as described above. Electrical contact is made between the polymeric material 106 and the electrode 104. The other side of the electropolymer film is placed in contact with an oxidation/reduction charge carrier (redox carrier molecule) in solution. The solution 202 can be formed in water, one or more organic solvents such as acetonitrile, gel, polymeric liquid, or other materials capable of electrical transport via charge carriers. In some cases, the solution includes additives such as, for example, electrolyte salts, acids, bases, etc. Electrode 108 is placed in contact with liquid solution 202, but not directly with the electropolymer film 106. Electrode 108 can be transparent, semi-transparent, or opaque. Electrode 108 can be made of, for example, metal or other conductor. Illumination of cell 200 results in a photovoltage across the two electrodes 104 and 108. When the circuit is complete, photocurrent results.

Light is absorbed by the porphyrin macrocycle of the electropolymer backbone. For a non-fullerene-containing electropolymer, the follow process occurs. Excitation energy migrates through the film to the region near the electrode (or near the liquid interface). The polymer excited state injects a charge (e.g., an electron) into the electrode (or into a redox carrier molecule in solution), leaving a charge of opposite sign (e.g., positive charge or hole) within the electropolymer film. This second charge migrates to the interface between the electropolymer and the solution 202, and is there transported into the solution phase via oxidation or reduction of a redox carrier molecule in solution (or into the electrode). The redox carrier can be, for example, quinone/hydroquinone. The oxidized or reduced redox carrier in solution 202 ultimately diffuses to the second electrode, and transfers the charge to that electrode by means of redox chemistry. A photovoltage between the electrodes is thus established. If the two electrodes are connected electrically through an electrical load 110, a photocurrent flows, and work is done. Creation of electron-hole pairs within the film is also possible, depending upon the redox characteristics of the particular polymer(s) used.

In the presence of an electropolymer material containing both porphyrin and fullerene (e.g., an electropolymer synthesized from compound 3), light is absorbed by both the porphyrin and the fullerene chromophores within the polymer. The porphyrin excited states donate electrons to the fullerenes, and the fullerene excited states can accept electrons from the porphyrin. In either case, a porphyrin-fullerene charge-separated state is formed. The electrons then migrate through the polymer and any associated conducting material to the solution interface where they are transferred to a redox carrier molecule in solution. The holes migrate to the electrode (or to the solution interface where they are transferred to a redox carrier molecule in solution). The oxidized or reduced redox carrier in solution ultimately diffuses to the second electrode, and transfers the charge to that electrode by means of redox chemistry. A photovoltage between the electrodes is thus established. If the two electrodes are connected electrically through an electrical load, a photocurrent flows, and work is done. Migration of excitation energy may also occur within the electropolymer.

The following examples illustrate various embodiments described herein.

EXAMPLES

Example 1

10-(4-Acetamidophenyl)-5,15-bis(2,4,6-trimethylphenyl)porphyrin (Compound 7)

To a flask was added 157 mg (0.250 mmol) of 10-bromo-5,15-bis(2,4,6-trimethylphenyl)porphyrin, (6), 1.06 g (5.00 mmol) of potassium phosphate tribasic, 314 mg (1.76 mmol) of 4-acetamidophenylboronic acid (supplied by Acros), and 70 mL of THF. The suspension was flushed with argon for 10 min, and then 39 mg (0.025 mmol) of tetrakis(triphenylphosphine)palladium(0) was added and the argon flushing procedure continued for an additional 10 min. The reaction mixture was then warmed to reflux under an argon atmosphere for 48 h. The solvent was evaporated at reduced pressure, the residue was redissolved in dichloromethane and washed with water, the organic phase was dried over sodium sulfate, and the solvent was once again evaporated at reduced pressure. The crude product was chromatographed on silica gel (dichloromethane/1% acetone) to give 124 mg (73% yield) of the desired porphyrin. $^1$H NMR (300 MHz) δ –2.89 (2H, s, N—H), 1.84 (12H, s, Ar—CH$_3$), 2.33 (3H, s, acetyl-CH$_3$), 2.67 (6H, s, Ar—CH$_3$), 7.29 (4H, s, Ar—H), 7.47 (1H, s, N—H), 7.85 (2H, d, J=8 Hz, Ar—H), 8.15 (2H, d, J=8 Hz, Ar—H), 8.72 (2H, d, J=5 Hz, β-H), 8.82 (4H, d, J=5 Hz, β-H), 9.26 (2H, d, J=5 Hz, β-H), 10.11 (1H, s, meso-H); MALDI-TOF-MS m/z calcd for C$_{46}$H$_{41}$N$_5$O$_1$ 679.33, obsd 679.33.

Example 2

10-(4-Aminophenyl)-5,15-bis(2,4,6-trimethylphenyl) porphyrin (Compound 2, Free Base)

A flask containing 100 mg (0.147 mmol) of 10-(4-acetamidophenyl)-5,15-bis(2,4,6-trimethylphenyl)porphyrin, 50 mL of trifluoroacetic acid, and 100 mL of concentrated hydrochloric acid was warmed to 80° C. After 18 h the acid was neutralized with concentrated aqueous ammonia, the purple porphyrin was extracted into dichloromethane and the solvent was evaporated at reduced pressure. The residue was then chromatographed on silica gel (dichloromethane/15-5% hexanes) to give 89 mg (95% yield) of the desired aminoporphyrin. $^1$H NMR (300 MHz) δ–2.87 (2H, s, N—H), 1.84 (12H, s, Ar—CH$_3$), 2.64 (6H, s, Ar—CH$_3$), 3.99 (2H, s, N—H), 7.04 (2H, d, J=8 Hz, Ar—H), 7.29 (4H, s, Ar—H), 7.99 (2H, d, J=8 Hz, Ar—H), 8.71 (2H, d, J=5 Hz, β-H), 8.81 (2H, d, J=5 Hz, β-H), 8.91 (2H, d, J=5 Hz, β-H), 9.24 (2H, d, J=5 Hz, β-H), 10.08 (1H, s, meso-H); MALDI-TOF-MS m/z calcd for C$_{44}$H$_{39}$N$_5$ 637.32, obsd 637.32; UV/vis (CH$_2$Cl$_2$) 414, 510, 545, 585, 642 nm.

Example 3

10-(4-tert-Butylphenylcarbamate)-5,15-bis(2,4,6-trimethylphenyl)porphyrin (Compound 8)

To a glass tube was added 250 mg (0.40 mmol) of 10-bromo-5,15-bis(2,4,6-trimethylphenyl)porphyrin (6), 1.28 g (4.00 mmol) of 4-(Boc-amino)benzeneboronic acid pinacol (supplied by Alfa Aesar), 1.70 g (8.00 mmol) of potassium phosphate tribasic, and 75 mL of THF. The suspension was flushed with a stream of argon for 10 min, 46 mg (0.04 mmol) of tetrakis(triphenylphosphine)palladium(0) was added, and the argon flushing was continued for an additional 10 min. The tube was sealed with a TEFLON® screw plug and the reaction mixture was warmed to 68° C. with vigorous stirring. After 20 h the reaction mixture was cooled and filtered through CELITE,® the residue was washed with dichloromethane, and the filtrate was concentrated. The residue was chromatographed on silica gel (dichloromethane/hexanes 2:1) to give 268 mg (91% yield) of the desired porphyrin. $^1$H NMR (300 MHz) δ–2.90 (2H, s, N—H), 1.64 (9H, s, —CH$_3$), 1.84 (12H, s, Ar—CH$_3$), 2.64 (6H, s, Ar—CH$_3$), 6.82 (1H, s, N—H), 7.29 (4H, s, Ar—H), 7.73 (2H, d, J=9 Hz, Ar—H), 8.13 (2H, d, J=9 Hz, Ar—H), 8.72 (2H, d, J=5 Hz, β-H), 8.82 (2H, d, J=4 Hz, β-H), 8.84 (2H, d, J=5 Hz, β-H), 9.26 (2H, d, J=4 Hz, β-H), 10.10 (1H, s, meso-H); MALDI-TOF-MS m/z calcd for C$_{49}$H$_{47}$N$_5$O$_2$ 737.37, obsd 737.37.

Example 4

10-(4-Aminophenyl)-5,15-bis(2,4,6-trimethylphenyl)porphyrin Compound 2, Free Base, Preparation 2)

To a flask containing 250 mg (0.34 mmol) of 10-(4-tert-butylphenylcarbamate)-5,15-bis(2,4,6-trimethylphenyl)porphyrin was added 30 mL of trifluoroacetic acid. The green solution was stirred under a nitrogen atmosphere for 15 min. The reaction mixture was then poured into dichloromethane (200 mL) and the resulting solution was washed with water (×2) and then aqueous sodium bicarbonate. After drying the organic phase over sodium sulfate, the solvent was evaporated at reduced pressure and the residue was chromatographed on silica gel (dichloromethane/15-10% hexanes) to give 203 mg (94% yield) of the aminoporphyrin. $^1$H NMR (300 MHz) δ–2.87 (2H, s, N—H), 1.84 (12H, s, Ar—H), 2.64 (6H, s, Ar—H), 4.00 (2H, s, N—H), 7.04 (2H, d, J=8 Hz, Ar—H), 7.29 (4H, s, Ar—H), 7.99 (2H, d, J=8 Hz, Ar—H), 8.71 (2H, d, J=5 Hz, β-H), 8.81 (2H, d, J=5 Hz, β-H), 8.91 (2H, d, J=5 Hz, β-H), 9.24 (2H, d, J=5 Hz, β-H), 10.08 (1H, s, meso-H); MALDI-TOF-MS m/z calcd for C$_{44}$H$_{39}$N$_5$ 637.32, obsd 637.32; UV/vis (CH$_2$Cl$_2$) 414, 510, 545, 585, 642 (nm).

Example 5

5-(4-Carboxymethylphenyl)-15-(2,4,6-trimethylphenyl)porphyrin (Compound 9)

A flask containing 1.76 g (12.00 mmol) of 2,2'-dipyrromethane, 0.89 mL (6.00 mmol) of mesitaldehyde, 0.98 g (6.00 mmol) of methyl 4-formylbenzoate, and 1.2 L of chloroform was flushed with a stream of argon for 15 min. Boron trifluoride-diethyl etherate (0.84 mL, 13.00 mmol) was added to the reaction mixture and the solution was stirred in the dark for 30 min. DDQ (4.0 g) was added and the stirring was continued for another 60 min. The reaction mixture was washed with sodium bicarbonate solution (×3) and concentrated by evaporation of the solvent at reduced pressure, and the residue was chromatographed on silica gel (dichloromethane/15-0% hexanes). The material isolated from the column was recrystallized from dichloromethane-methanol to give 1.03 g (22% yield) of the desired porphyrin. $^1$H NMR (300 MHz) δ–3.09 (2H, s, N—H), 1.85 (6H, s, Ar—CH$_3$), 2.66 (3H, s, Ar—CH$_3$), 4.14 (3H, s, —COOCH$_3$), 7.32 (2H, s, Ar—H), 8.34 (2H, d, J=8 Hz, Ar—H), 8.49 (2H, d, J=8 Hz, Ar—H), 8.90 (2H, d, J=5 Hz, β-H), 9.00 (2H, d, J=5 Hz, β-H), 9.33 (2H, d, J=5 Hz, β-H), 9.38 (2H, d, J=5 Hz, δ-H), 10.26 (2H, s, meso-H); MALDI-TOF-MS m/z calcd for C$_{37}$H$_{30}$N$_4$O$_2$ 562.24, obsd 562.24.

Example 6

5-(4-Formylphenyl)-15-(2,4,6-trimethylphenyl)porphyrin (Compound 10)

A flask containing 200 mg (0.35 mmol) of 5-(4-carboxymethylphenyl)-15-(2,4,6-trimethylphenyl)porphyrin, and 70 mL of tetrahydrofuran was cooled to 5-10° C. before lithium aluminum hydride was added in small quantities. The progress of the reaction was followed by TLC (silica gel/dichloromethane). Once all the porphyrin ester had been consumed, ice was added (cautiously) to the reaction mixture. The solvent was distilled under reduced pressure and the residue was redissolved in dichloromethane. The resulting solution was dried over sodium sulfate and then concentrated by distillation at reduced pressure. The compound was used without further purification.

The porphyrin alcohol was dissolved in 50 mL of dichloromethane and stirred as small portions of activated manganese dioxide were added. The course of the reaction was followed by TLC (silica gel/dichloromethane). Once the conversion was complete, the reaction mixture was filtered through CELITE® and the filtrate was concentrated by evaporation of the solvent at reduced pressure. The residue was chromatographed on silica gel (dichloromethane/15-5% hexanes) to give 157 mg (83% yield) of the expected porphyrin. $^1$H NMR (300 MHz) δ–3.09 (2H, s, N—H), 1.84 (6H, s, Ar—CH$_3$), 2.66 (3H, s, Ar—CH$_3$), 7.32 (2H, s, Ar—H), 8.32 (2H, d, J=8 Hz, Ar—H), 8.44 (2H, d, J=8 Hz, Ar—H), 8.90 (2H, d, J=4 Hz, β-H), 8.99 (2H, d, J=4 Hz, β-H), 9.34 (2H, d, J=5 Hz, β-H), 9.40 (2H, d, J=5 Hz, β-H), 10.28 (2H, s, meso-H), 10.41 (1H, s, —CHO); MALDI-TOF-MS m/z calcd for C$_{36}$H$_{28}$N$_4$O$_1$ 532.23, obsd 532.22.

Example 7

10-Bromo-5-(4-formylphenyl)-15-(2,4,6-trimethylphenyl)porphyrin (Compound 11)

To a flask containing 150 mg (0.282 mmol) of 5-(4-formylphenyl)-15-(2,4,6-trimethylphenyl)porphyrin, and 20 mL of chloroform was added 50 mg (0.282 mmol) of N-bromosuccinimide. The reaction mixture was stirred for 30 min under a nitrogen atmosphere. The solvent was evaporated at reduced pressure and the residue was chromatographed on silica gel (dichloromethane/hexanes 4:3 to 2:1) to give 119 mg (69% yield) of the monobrominated porphyrin. $^1$H NMR (300 MHz) δ−2.91 (2H, s, N—H), 1.83 (6H, s, Ar—CH$_3$), 2.65 (3H, s, Ar—CH$_3$), 7.31 (2H, s, Ar—H), 8.30 (2H, d, J=8 Hz, Ar—H), 8.37 (2H, d, J=8 Hz, Ar—H), 8.81 (2H, d, J=5 Hz, β-H), 8.85 (1H, d, J=2 Hz, β-H), 8.87 (1H, d, J=2 Hz, β-H), 9.25 (1H, d, J=6 Hz, β-H), 9.29 (1H, d, J=6 Hz, β-H), 9.69 (1H, d, J=6 Hz, β-H), 9.74 (1H, d, J=6 Hz, β-H), 10.14 (1H, s, meso-H), 10.40 (1H, s, —CHO); MALDI-TOF-MS m/z calcd for C$_{36}$H$_{27}$N$_4$O$_1$Br$_1$ 610.14, obsd 610.14.

Example 8

5-(4-Formylphenyl)-10-(4-tert-butylphenylcarbamate)-15-(2,4,6-trimethylphenyl)porphyrin (Compound 12)

To a glass tube was added 110 mg (0.180 mmol) of 10-bromo-5-(4-formylphenyl)-15-(2,4,6-trimethylphenyl) porphyrin, 574 mg (1.80 mmol) of 4-(Boc-amino)benzeneboronic acid pinacol, 764 mg (3.60 mmol) of potassium phosphate tribasic, and 35 mL of THF. The suspension was flushed with argon for 10 min, 21 mg (0.018 mmol) of tetrakis-(triphenylphosphine)palladium(0) was added, and the argon flushing was continued. After 10 min the tube was sealed with a TEFLON® screw plug and the reaction mixture was warmed to 68° C. for 17 h. Upon cooling, the reaction mixture was filtered through CELITE,® the residue was washed well with dichloromethane, and the filtrate was concentrated by distillation at reduced pressure. The impure material was chromatographed on silica gel (hexanes/15-20% ethylacetate) to give 114 mg (87% yield) of the desired porphyrin. $^1$H NMR (300 MHz) δ−2.94 (2H, s, N—H), 1.64 (9H, s, —CH$_3$), 1.84 (6H, s, Ar—CH$_3$), 2.64 (3H, s, Ar—H), 6.85 (1H, s, N—H), 7.30 (2H, s, Ar—H), 7.67 (2H, d, J=8 Hz, Ar—H), 8.13 (2H, d, J=8 Hz, Ar—H), 8.29 (2H, d, J=7 Hz, Ar—H), 8.40 (2H, d, J=7 Hz, Ar—H), 8.75 (1H, d, J=4 Hz, β-H), 8.80 (1H, d, J=5 Hz, β-H), 8.85 (1H, d, J=4 Hz, β-H), 8.88 (1H, d, J=5 Hz, β-H), 8.91 (1H, d, J=2 Hz, β-H), 8.93 (1H, s, J=2 Hz, δ-H), 9.28 (1H, d, J=5 Hz, β-H), 9.33 (1H, d, J=5 Hz, β-H), 10.17 (1H, s, meso-H), 10.39 (1H, s, —CHO); MALDI-TOF-MS m/z calcd for C$_{47}$H$_{41}$N$_5$O$_3$ 723, obsd 723.

Example 9

P—C$_{60}$ Dyad (Compound 3)

To a tube was added 100 mg (0.138 mmol) of 5-(4-formylphenyl)-10-(4-tert-butylphenylcarbamate)-15-(2,4,6-trimethylphenyl)porphyrin, 200 mg (0.276 mmol) of C$_{60}$, 123 mg (1.381 mmol) of sarcosine, and 40 mL of toluene. The suspension was flushed with argon for 10 min, the tube was sealed with a TEFLON® screw plug and the reaction mixture was warmed to 110° C. for 16 h. The solvent was evaporated at reduced pressure and the residue was chromatographed on silica gel (carbon disulfide/dichloromethane/hexanes 100:85: 15 to carbon disulfide/dichloromethane 1:2) to give 80 mg (39% yield) of the dyad 13. $^1$H NMR (300 MHz) δ−3.03 (2H, s, N—H), 1.62 (9H, s, —CH$_3$), 1.82 (6H, s, Ar—CH$_3$), 2.61 (3H, s, Ar—CH$_3$), 3.10 (3H, s, N—CH$_3$), 4.46 (1H, d, J=9 Hz, pyrrolid-H), 5.04 (1H, d, J=9 Hz, pyrrolid-H), 5.20 (1H, s, pyrrolid-H), 6.76 (1H, s, N—H), 7.24 (2H, s, Ar—H), 7.70 (2H, d, J=9 Hz, Ar—H), 8.07 (2H, d, J=8 Hz, Ar—H), 8.17 (2H, brd s, Ar—H), 8.24 (2H, d, J=7 Hz, Ar—H), 8.66 (2H, d, J=4 Hz, β-H), 8.77 (2H, d, J=5 Hz, β-H), 8.80 (2H, d, J=5 Hz, β-H), 9.22 (2H, d, J=4 Hz, β-H), 10.07 (1H, s, meso-H); MALDI-TOF-MS m/z calcd for C$_{109}$H$_{46}$N$_6$O$_2$ 1470.37, obsd 1470.39.

A solution including 60 mg (0.041 mmol) of dyad 13 and 20 mL of trifluoroacetic acid was stirred under an argon atmosphere for 15 min. It was then diluted with methylene chloride (100 mL) and washed with water and then aqueous sodium bicarbonate until all the acid had been neutralized. The solvent was evaporated and the residue was chromatographed on silica gel (flash column, methylene chloride/carbon disulphide 3:1 to 6:1) to give 52 mg (93% yield) of dyad 3. $^1$H NMR (400 MHz, CDCl$_3$/CS$_2$) δ−2.98 (2H, s, N—H), 1.86 (6H, s, Ar—CH$_3$), 2.66 (3H, s, Ar—CH$_3$), 3.17 (3H, s , N—CH$_3$), 3.98 (2H, s, —NH$_2$), 4.46 (1H, d , J=9 Hz, pyrrolid.—H), 5.14 (1H, d, J=9 Hz, pyrrolid. —H), 5.30 (1H, s, pyrrolid. —H), 7.01 (2H, d, J=8 Hz, Ar—H), 7.27 (2H, s, Ar—H partially obscured by CDCl$_3$), 7.94 (2H, d, J=7 Hz, Ar—H), 8.23 (2H, brd. s, Ar—H), 8.29 (2H, d, J=7 Hz, Ar—H), 8.68 (2H, d, J=4 Hz, β-H), 8.78 (2H, d, J=4 Hz, β-H), 8.88 (2H, d, J=5 Hz, β-H), 9.23 (2H, d, J=5 Hz, β-H), 10.07 (1H, s, meso-H); MALDI-TOF-MS m/z calcd. for C$_{104}$H$_{38}$N$_6$ 1370.3, obsd. 1370.3; Uv/vis (CH$_2$Cl$_2$) 416, 511, 546, 586, 640, 703 (nm).

Example 10

Polymerization of Compound 2 (Free Base)

Figure 3:
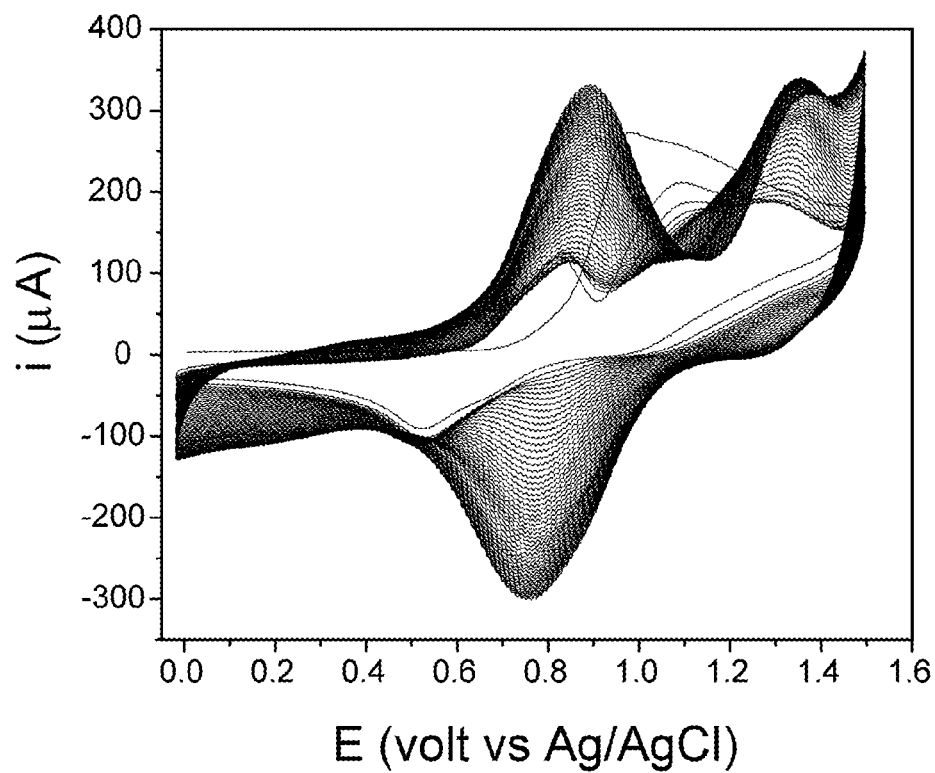
FIG. 3 shows a plot of current versus applied voltage for the electropolymerization of compound 2.

FIG. 3 shows the course of electropolymerization of compound 2 (free base) on ITO over approximately 50 cycles of the type described above. The voltage range per cycle was 0.0 V to 1.5 V. With each voltage cycle, the current increased by approximately the same amount after the first few cycles. This shows that the electropolymer is conductive, that each sweep to higher voltage results in oxidation of most or all of the polymer film already on the electrode prior to deposition of a new layer of electropolymer, and that each return sweep to lower voltage results in reduction of the oxidized polymer.

Figure 4:
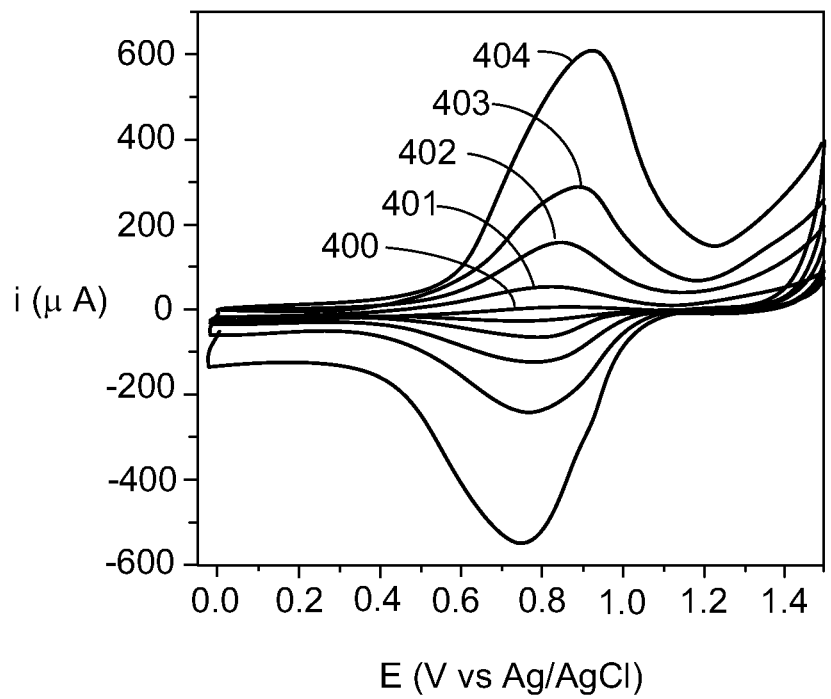
FIG. 4 shows a stacked plot of current versus applied voltage as a function of voltage sweep rate for the polymer produced from compound 2.

FIG. 4 shows the cyclic voltammogram obtained from an ITO electrode with a porphyrin polymer film formed from compound 2 (free base) in acetonitrile, with tetrabutylammonium hexafluorophosphate as a supporting electrolyte. The counter electrode was Pt, and the reference electrode was Ag/AgCl. Plots 400, 401, 402, 403, and 404 correspond to scan rates of 20, 50, 100, 200, and 500 mV/s, respectively.

Figure 5:
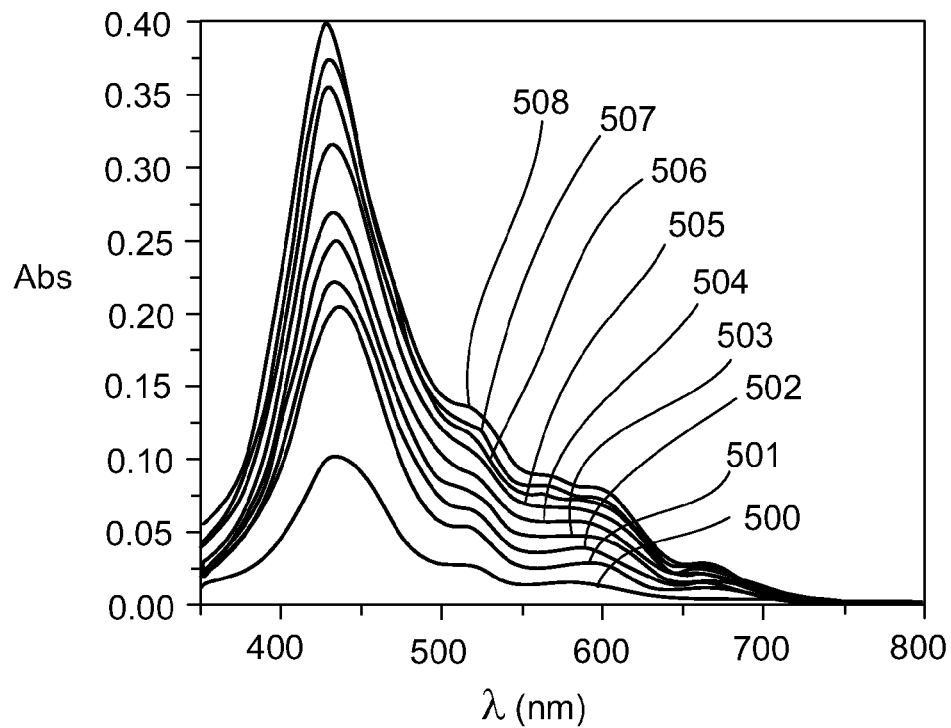
FIG. 5 shows a stacked plot of absorbance as a function of number of electropolymerization cycles.

FIG. 5 shows the UV-VIS absorbance of the porphyrin polymer formed from compound 2 (free base) on transparent ITO. After the first few cycles, the increase in porphyrin absorbance is linear with the number of cycles, indicating that the conductivity does not decrease with increasing polymer thickness. Plots 500, 501, 502, 503, 504, 505, 506, 507, and 508 refer to absorbance of 5, 10, 15, 20, 26, 31, 36, 41, and 46 layers, respectively, with a maximum absorbance of about 0.4. Additional layers were made with up to 100 cycles, yielding an absorbance of approximately 2 in the 430 nm region.

The MALDI-TOF mass spectrum of an extract from the polymer containing short segments yields ions consistent with a polymer containing monomer units similar to compound 2 (free base), but lacking two hydrogen atoms, as required for the polymer shown formula (XV). Additionally, the infrared spectrum of the polymer is consistent with the absence of a meso hydrogen atom, whereas the spectrum of compound 2 is consistent with the presence of a meso hydrogen atom.

Example 11

Polymerization of Compound 2, M=Zn

Compound 2, with M=Zn, was synthesized in a procedure similar to that discussed in Example 10 to yield a conducting, metal-containing polymer.

Example 12

Preparation of Polymer with M=Zn from Compound 2 (Free Base)

Zinc was incorporated into the polymer prepared in Example 10 by soaking a film-covered electrode in a dimethylformamide solution of zinc acetate.

Example 13

Solid Film Solar Cell (Non-Fullerene-Containing)

Porphyrinic polymer material was polymerized as described above from compound 2 (free base) on ITO. The side of the polymer film opposite the ITO was contacted with a circular mercury contact having a diameter of about 3 mm. A Keithley 2400 source-meter was used for all measurements. The positive terminal of the Keithley was connected to the ITO and the negative terminal was connected to the mercury. The light source used was a green laser pointer (532 nm). All photocurrent measurements were taken for 60 seconds. The light source was off for the first 30 seconds and on for the last 30 seconds.

Figure 6:
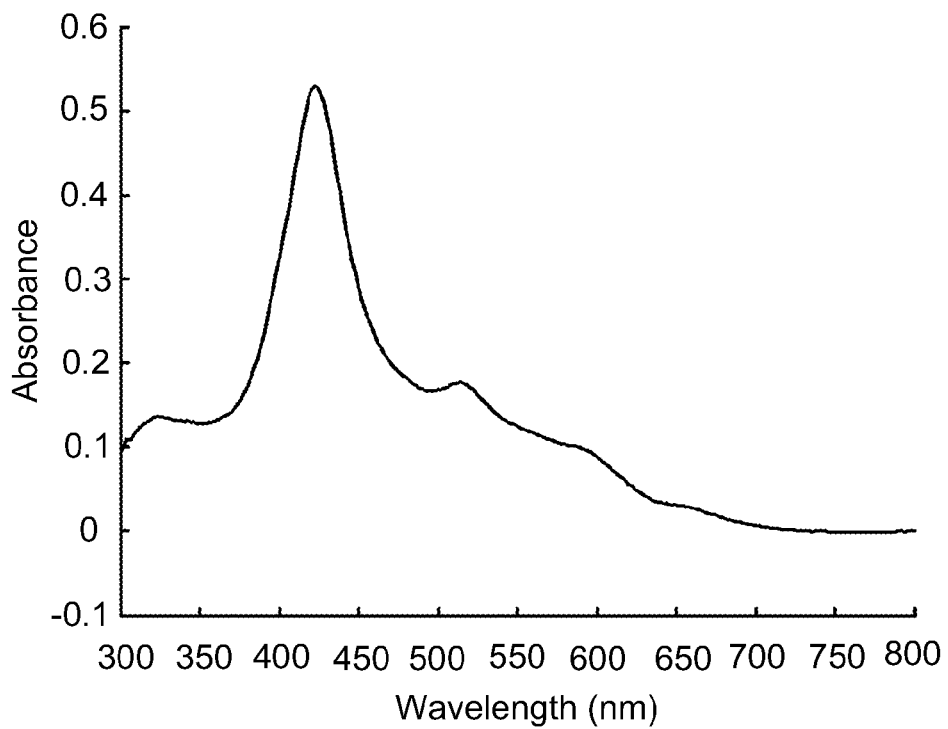
FIG. 6 is an absorption spectrum of an electrode coated with a porphyrin polymer film.
Figure 7:
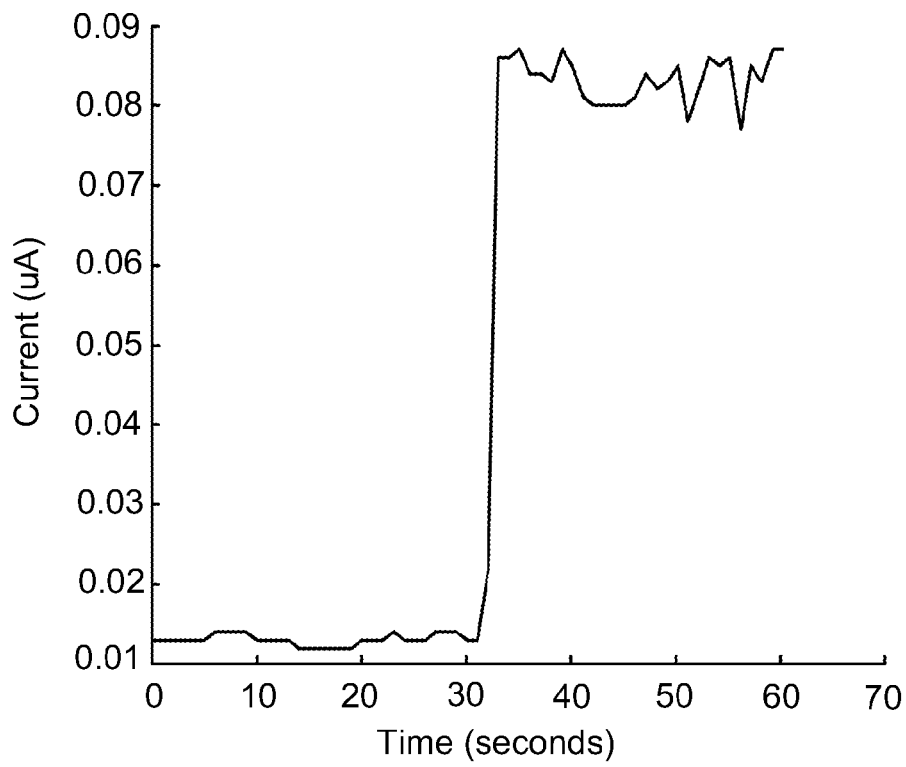
FIG. 7 is a plot of photocurrent of a solid film solar cell with a porphyrin polymer film.
Figure 8:
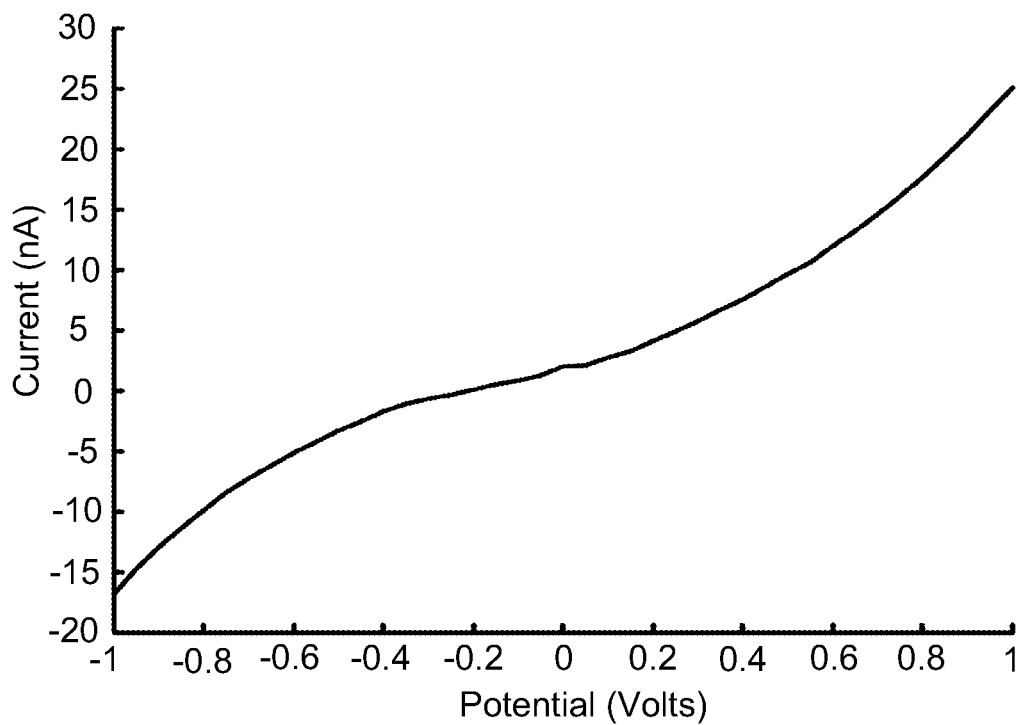
FIG. 8 is a current-voltage curve for a solid film solar cell with a porphyrin polymer film in the absence of illumination.

FIG. 6 shows the absorption spectrum of an ITO electrode bearing the porphyrin polymer film prepared from compound 2 (free base). FIG. 7 shows the photocurrent for such an electrode, measured as described above. The photocurrent was near zero in the dark, but increased to about 85 nA when the light was turned on at about 30 seconds, demonstrating photovoltaic behavior by producing photocurrent upon illumination. FIG. 8 is a plot of cell current vs. applied voltage, taken on the same cell in the dark. Note that it is not symmetric, indicating that the magnitude of the current at a given voltage is a function of the direction of the applied voltage. That is, the film has some of the characteristics of a diode.

Example 14

Solid Film Solar Cell (Fullerene-Containing)

Figure 9:
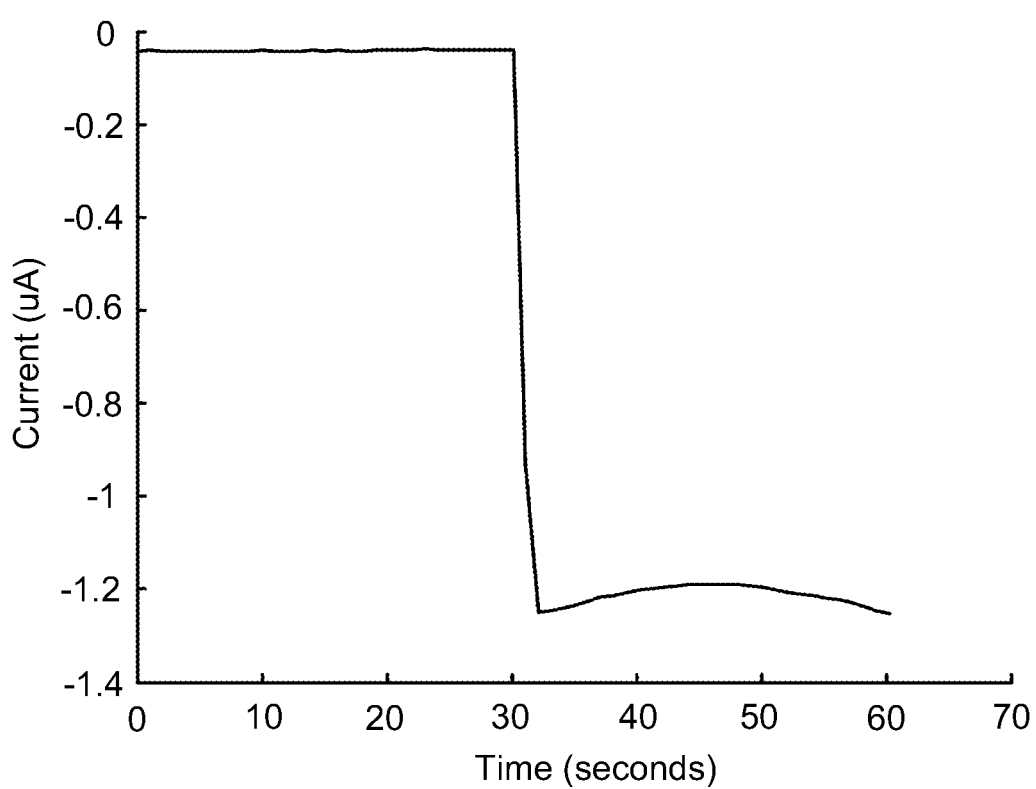
FIG. 9 is a plot of photocurrent for a porphyrin-fullerene polymer film.

A solid film solar cell was prepared as described in Example 13 with a porphyrin-fullerene polymer electropolymerized from compound 3 (free base) on ITO. FIG. 9 shows the photocurrent generated the porphyrin-$C_{60}$ polymer film. The conditions were the same as discussed in Example 13, except that the light source was a Fiber-Lite high intensity illuminator series 180 from Dolan-Jenner Industries, Inc. The photocurrent demonstrates that the device functions as a photovoltaic. Note that the direction of the photocurrent is opposite to that obtained with the polymer made from the porphyrin alone. Note, however, that FIG. 7 and FIG. 9 were obtained with different light sources. Therefore, the amplitudes of the photocurrents cannot be compared directly.

Example 15

Redox-Solution-Containing Solar Cell (Non-Fullerene-Containing)

Thin films of porphyrin polymer were grown on ITO conductive glass by electropolymerization of a solution containing 0.60 mM 5-(4-aminophenyl)-10,20-bis(2,4,6-trimethylphenyl)porphyrin (compound 2, free base) and 100 mM tetrabutylammonium hexafluorophosphate in acetonitrile solvent. Electropolymerization occurred while cycling the potential on the ITO between –0.1 V and 1.5 V at 200 mV/sec using a silver wire reference electrode and platinum gauze counter electrode. The resulting ITO/polymer electrodes were sandwiched near a platinized FTO conductive glass second electrode at a spacing of 0.25 µm using heat-seal plastic. Predrilled holes in the FTO electrode allowed introduction of solution into the gap between electrodes. An acetonitrile solution of 100 mM 1,4-benzoquinone and 1.0 mM 1,4-hydroquinone as redox carrier, with 150 mM tetrabutylammonium hexafluorophosphate as supporting electrolyte, was introduced into the space between the electrodes.

Figure 10:
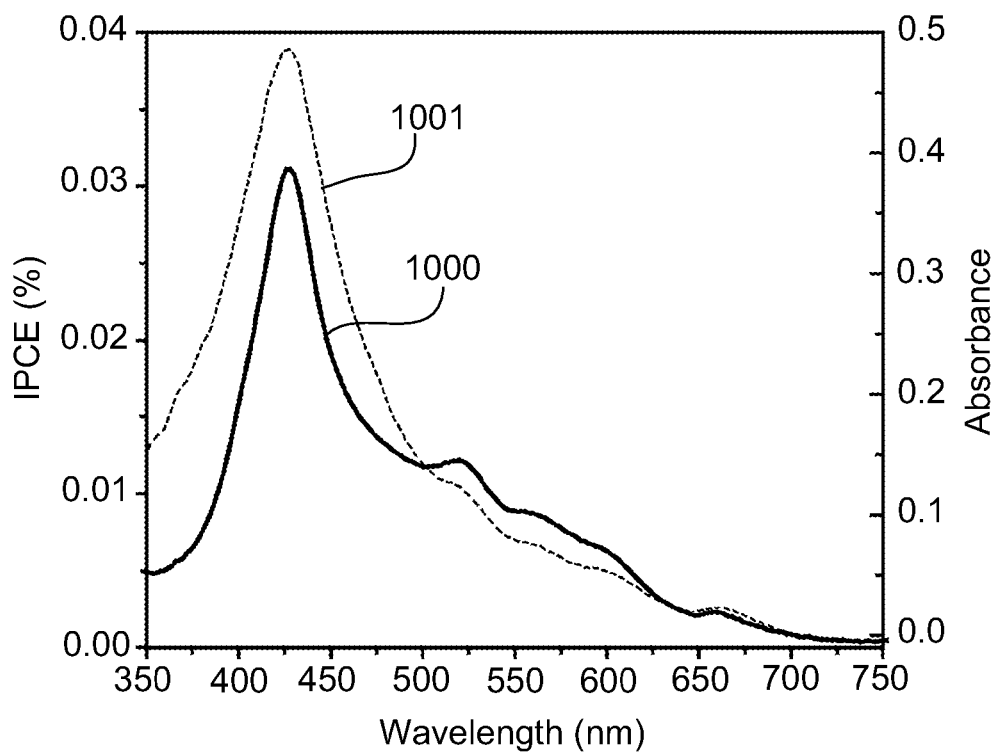
FIG. 10 depicts an absorbance spectrum of a polymer coated electrode and incident photon to current efficiency (IPCE) of the corresponding redox-solution-containing solar cell.

Photoinduced electrical current was determined using a xenon lamp light source and monochromator. Electrical current was measured under illumination and in the dark, and the dark current was subtracted to obtain the photocurrent. FIG. 10 shows the results of illumination of the cell. Plot 1000 is the absorption spectrum of the transparent electrode as determined on a UV-Vis spectrophotometer. Plot 1001 is the incident photon to current efficiency (IPCE) as determined from measurements of the cell, electrode, and light source. The IPCE represents the fraction of photons incident on the electrode that give rise to electrons in the external circuit.

As indicated by FIG. 10, the cell generated photovoltage and photocurrent upon exposure to light, and therefore performed as a photovoltaic or solar cell. The IPCE as a function of wavelength resembles the absorption spectrum of the transparent electrode, showing that the light giving rise to the photovoltage and photocurrent was absorbed by the electropolymerized porphyrinic material on the electrode surface. Photocurrent was generated by light from at least 350 nm to beyond 700 nm, representing a significant fraction of the solar spectrum on Earth. The electrons flowed from the electropolymerized porphyrinic material into the solution by reduction of benzoquinone, into the FTO non-illuminated electrode, through the external circuit, and into the ITO transparent electrode and the electropolymerized porphyrinic material film.

Example 16

Redox-Solution-Containing Solar Cell (Fullerene-Containing)

A redox-solution-containing solar cell was constructed with a film grown from porphyrin-fullerene compound 3 (free base). This cell generated greater photocurrent and photovoltage than the cell described in Example 15.

It is understood that the foregoing detailed description and accompanying Examples are merely illustrative and are not to be taken as limitations upon the scope of the invention, which is defined by the appended claims. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A porphyrin polymer having the formula:

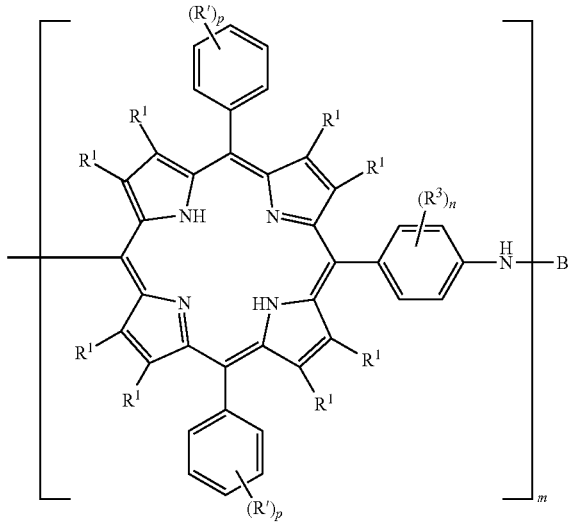

wherein:
- m is an integer greater than 2, wherein m indicates the number of porphyrin monomers in the porphyrin polymer,
- each $R^1$ is independently —H, -alkyl, or -alkenyl, wherein $R^1$ is optionally substituted with one or more groups which are each independently R, or any two $R^1$ on adjacent carbon atoms form a fused phenyl group which is optionally substituted by one or more R groups, and
- $R^3$ is -halogen, -alkyl, -aryl, -cycloalkyl, -heterocyclyl, or -heteroaryl, wherein $R^3$ is optionally substituted with one or more R groups, and n is 0, 1, 2, 3, or 4,
- each R is independently -halogen, -alkyl, -aryl, -cycloalkyl, -heterocyclyl, -heteroaryl, —$OR^4$, —$SR^4$, —$N(R^4)_2$, —$C(O)R^4$, —$C(O)OR^4$, —$C(O)N(R^4)_2$, —$OC(O)R^4$, —$OC(O)OR^4$, —$OC(O)N(R^4)_2$, —$N(R^4)C(O)R^4$, —$N(R^4)C(O)OR^4$, —$N(R^4)C(O)N(R^4)_2$, —$S(O)_2R^4$, —$S(O)_2N(R^4)_2$, or —$S(O)_2OR^4$,
- each R' is independently -halogen, -alkyl, -aryl, -cycloalkyl, -heterocyclyl, -heteroaryl, —$SR^4$, —$N(R^4)_2$, —$C(O)R^4$, —$C(O)OR^4$, —$C(O)N(R^4)_2$, —$OC(O)R^4$, —$OC(O)OR^4$, —$OC(O)N(R^4)_2$, —$N(R^4)C(O)R^4$, —$N(R^4)C(O)OR^4$, —$(R^4)C(O)N(R^4)_2$, —$S(O)_2R^4$, —$S(O)_2N(R^4)_2$, —$S(O)_2OR^4$, or $R^F$,
- $R^F$ is -L-cycloalkyl or -L-heterocyclyl, and wherein the cycloalkyl and heterocyclyl are optionally substituted with $R^5$ groups,
- each $R^4$ is independently —H or -alkyl,
- each $R^5$ is independently R, or two $R^5$ groups on adjacent carbon atoms form a fused aryl, -heteroaryl-, -heterocyclyl-, -cycloalkyl- or -fullerenyl-,
- L is a bond, -$L^1$-, -$L^1$-alkyl-, or -$L^1$-alkyl-$L^1$-, wherein $L^1$ is —C(O)O—, —OC(O)—, —$N(R^4)C(O)$—, —$C(O)N(R^4)$—, —O—, —S—, —$N(R^4)$—, —OC(O)O—, —$OC(O)N(R^4)$—, —$N(R^4)C(O)O$—, or —$N(R^4)C(O)N(R^4)$—, and
- each p is independently 0, 1, 2, 3, 4, or 5.

2. The polymer according to claim 1, wherein each p is independently 0, 1, 2, or 3, and each R' is independently -halogen or -alkyl.

* * * * *

UNITED STATES PATENT AND TRADEMARK OFFICE
CERTIFICATE OF CORRECTION

PATENT NO. : 8,669,359 B2  Page 1 of 1
APPLICATION NO. : 12/552187
DATED : March 11, 2014
INVENTOR(S) : John Devens Gust, Jr. et al.

It is certified that error appears in the above-identified patent and that said Letters Patent is hereby corrected as shown below:

Title page, Column 2 (Other Publications), line 24, delete "functionazlied" and insert
-- functionalized --.

In the Claims

Column 37, lines 10-30, in Claim 1, delete " 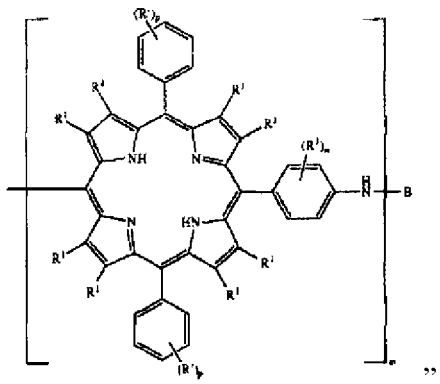 "

and insert -- 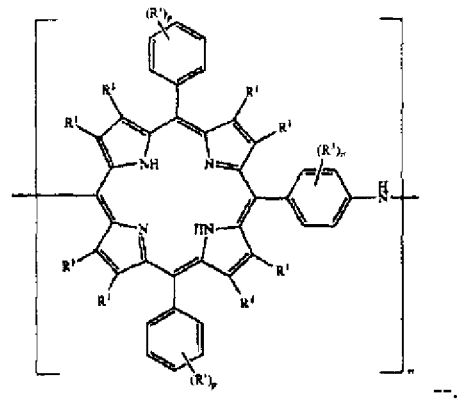 --.

Signed and Sealed this
Twenty-sixth Day of August, 2014

Michelle K. Lee
*Deputy Director of the United States Patent and Trademark Office*